US010308893B2

(12) United States Patent
Nates et al.

(10) Patent No.: US 10,308,893 B2
(45) Date of Patent: Jun. 4, 2019

(54) ORGANIC MATERIAL PROCESSING SYSTEM

(71) Applicants: Enrique Maya Nates, Vallejo, CA (US); Matthew Gaines Richmond, Benicia, CA (US); Sergio Nates Maya, Mexico City (MX)

(72) Inventors: Enrique Maya Nates, Vallejo, CA (US); Matthew Gaines Richmond, Benicia, CA (US); Sergio Nates Maya, Mexico City (MX)

(73) Assignee: Xpert Xtractors Inc., Benecia, CA (US)

( * ) Notice: Subject to any disclaimer, the term of this patent is extended or adjusted under 35 U.S.C. 154(b) by 0 days.

(21) Appl. No.: 15/743,599

(22) PCT Filed: Jul. 14, 2016

(86) PCT No.: PCT/US2016/042345
§ 371 (c)(1),
(2) Date: Jan. 10, 2018

(87) PCT Pub. No.: WO2017/015065
PCT Pub. Date: Jan. 26, 2017

(65) Prior Publication Data
US 2018/0201871 A1     Jul. 19, 2018

Related U.S. Application Data

(60) Provisional application No. 62/193,707, filed on Jul. 17, 2015, provisional application No. 62/207,122, filed on Aug. 19, 2015.

(51) Int. Cl.
*C11B 1/10*      (2006.01)
*B01D 11/02*    (2006.01)
(Continued)

(52) U.S. Cl.
CPC ............ *C11B 1/10* (2013.01); *B01D 11/0273* (2013.01); *B01D 11/0288* (2013.01);
(Continued)

(58) Field of Classification Search
CPC ... C11B 1/10; C11B 1/108; C11B 3/00; C11B 13/00; B01D 11/0273; B01D 11/0288
See application file for complete search history.

(56) References Cited

U.S. PATENT DOCUMENTS

2004/0147769 A1    7/2004  Davis
2008/0262253 A1*  10/2008  Nakamura ................ C11B 1/06
554/9
(Continued)

*Primary Examiner* — Yate' K Cutliff
(74) *Attorney, Agent, or Firm* — Lamon Patent Services; Cynthia S. Lamon

(57) ABSTRACT

An extraction system comprises an extraction chamber having an end cap at an one end accepting organic matter and gas or liquid solvent. A collection vessel is attached below the extraction chamber, a viewing vessel is sealed at an acute angle to a sidewall of the collection vessel enabling visual inspection at the collection plate. A gas tank is connected to the extraction chamber introducing solvent and a frame supports chamber by axles fixedly mounted on opposite sides of the extraction chamber, said axles supported by the frame structure enabling free rotation of the chamber about the axles. After gas is introduced to the organic matter, the extraction chamber is rotated vigorously about the axis, the one end is then connected to the open upper end of the collection vessel, and a lipid yield is collected at the collection plate.

22 Claims, 16 Drawing Sheets

(51) Int. Cl.
*C11B 13/00* (2006.01)
*C11B 3/00* (2006.01)

(52) U.S. Cl.
CPC .............. *C11B 1/108* (2013.01); *C11B 13/00* (2013.01); *C11B 3/00* (2013.01); *Y02W 30/74* (2015.05)

(56) References Cited

U.S. PATENT DOCUMENTS

| | | |
|---|---|---|
| 2010/0191007 A1 | 7/2010 | Davis |
| 2013/0098751 A1* | 4/2013 | Eyer ........................ C10B 49/06 201/2 |
| 2014/0193303 A1* | 7/2014 | Ellis ................... B01D 11/0203 422/119 |

* cited by examiner

ORGANIC MATERIAL PROCESSING SYSTEM

CROSS-REFERENCE TO RELATED DOCUMENTS

The present invention claims priority to a U.S. provisional patent application Ser. No. 62/193,707 entitled Angled Degree Viewing Port for Biomass Distilling Machine filed on Jul. 17, 2015 and to a U.S. provisional patent application Ser. No. 62/207,122 entitled Spinning Function for Live Fresh Plant Maceration in a Biomass Distilling Machine filed on Aug. 19, 2015, disclosure of which is incorporated herein at least by reference.

BACKGROUND OF THE INVENTION

1. Field of the Invention

The present invention is in the field of biomass material processing and extraction systems and pertains particularly to methods and apparatus for reducing time and workload relative to material processing.

2. Discussion of the State of the Art

In the field of bio-mass extraction systems (Organic Material Processors) closed loop distillation and extraction systems are available for processing biomass to isolate or separate essential oils and other desirable organic products for recovery from introduced organic materials such as plant materials. Maceration is the use of gasses or liquid solvents to soften and separate certain constituents from the overall plant matter introduced for processing. The definitions of biomass include, basically any type of organic matter. Solvents may be a variety of agents that might be introduced into a maceration chamber or vessel in gaseous and or in liquid phases or states. The term yield is often used to describe the separated constituents after purging or removal of any leftover contaminants (typically including the solvent used in maceration).

Some systems are open systems meaning that there may be an outside exposure to any solvents used to process the bio-materials. Open systems are inherently dangerous when flammable solvents or isolative solutions are employed under certain less than optimal conditions and explosions have resulted including injury to workers. Closed loop systems are preferable but not entirely danger free as process miscalculations or missteps can still result in problems. Other challenges in processing biomass include the removal of contaminants from extracted materials. Still other challenges exist such as ability to determine safely when material processing is exhausted for a batch of introduced materials. Moreover, negative factors may affect the overall process such as lack of safety protocols, lack of clear indication when a process is completed, large number of steps to execute during a process, requirement of more than one worker conducting a process, and so on. These factors may weigh heavily as to the commercial viability of extracting a constituent such as lipids from a commercial grade mass or batch of bio materials.

Therefore, what is clearly needed is a biomass distillation system or broadly an organic material processing system and methods that address and solves the challenges mentioned above.

BRIEF SUMMARY OF THE INVENTION

The present invention provides a novel extraction system comprising a vertically oriented cylindrical extraction chamber having a hollow inner volume, an end cap at an one end of the extraction chamber enabled to accept organic matter into the chamber, and at least one inlet valve at a second end, opposite the one end, enabled to inject a gas or liquid solvent into the inner volume. A cylindrical collection vessel is centered and positioned below the one end cap of the extraction chamber, the collection vessel including a closed lower end supported by a collection plate, and an open upper end enabled to connect to the one end cap of the extraction chamber, an interior volume and a viewing vessel with an open lower end sealed at an angle to an upper portion of a sidewall of the collection vessel. The viewing vessel also includes an open upper end and an elongated viewing tube through the sidewall ending at a viewing port with a lens, the viewing tube enables visual inspection through the lens and tube of the interior volume of the collection vessel at the collection plate.

A gas introduction and recovery tank is connected to the extraction chamber via a first ingress fitting enabled to couple by conduit to a first egress fitting positioned at the upper end of the collection vessel to recover used extraction gas, and a second egress fitting on the tank enabled to connect by conduit to the at least one inlet valve introducing gas into the extraction chamber.

A frame structure supports the extraction chamber by a first and second axle, one each fixedly mounted on opposite sides of the extraction chamber at a balanced center point along a length between the one end and second end of the extraction chamber, said axles supported by the frame structure enabled to hold the chamber at a height from ground enabling free rotation of the chamber about the axles.

The process proceeds after introduction of the organic matter into the extraction chamber, with the end cap sealed, the first ingress and egress fittings are connected via the conduit and extraction gas is introduced in a quantity enabling at least lipid removal from the organic matter, said process influenced by rotating the extraction chamber vigorously about the axis, the one end is then connected to the open upper end of the collection vessel, via the end cap, and a lipid yield is collected at the collection plate while simultaneously recovering the extraction gas to the tank via the conduit connected second ingress and egress fittings and viewing quantity and quality of the yield via the viewing vessel.

In one embodiment the extraction system includes a filter plate positioned between the extraction chamber and collection vessel via an inlet opening removably attached to the end cap of the extraction chamber and an exit opening removably attached to the open upper end of the collection vessel, said filter removing contaminates from the yield. All connections between the extraction chamber, collection vessel and filter plate are sealed connections provided by clamp and gasket assemblies. An alternative embodiment provides a turn wheel used to mechanically rotate the extraction chamber via the axles.

A temperature controlled heater is positioned, in one embodiment, adjacent to and directly below the collection plate passively aiding in removal of at least gas and water contaminates from the yield. Additional heating occurs at the extraction chamber, collection vessel and collection plate, alternately, to aid in passively moving and extracting used gas from the system.

In an alternative embodiment, or simultaneously with the heating process, above, a vacuum pump is connected to the conduit between the second ingress and egress fittings in order to aid in gas recovery.

In one embodiment the angle of attachment of the viewing vessel is an acute angle, enabling the open upper end to extend outwards and upwards toward the open upper end of the collection vessel. Additionally, all components are connected, a closed system is created that is enabled to hold a negative or positive atmospheric pressure.

A method of using the extraction system is provided comprising the steps of placing the organic matter within a hollow inner volume of an cylindrical extraction chamber having an end cap at one end, an inlet valve at a second end, opposite the one end, enabled to inject a gas or liquid solvent into the inner volume; sealing the end cap with clamp and gasket assemblies achieving an airtight extraction chamber and introducing a gas solvent to the inner volume by coupling conduit to an ingress fitting at the inlet valve from a first egress fitting connected to a tank holding a reserve of solvent; removing the ingress fitting from the inlet valve and agitating and macerating the organic matter and solvent by rotating the extraction chamber via a first and second axle one each fixedly mounted on opposite sides of the extraction chamber at a balanced center point along a length between the upper and lower ends of the extraction chamber, said axles supported by a frame enabled to hold the chamber at a height from ground enabling free rotation of the chamber about the axles.

The solvent is then collected along with lipid yield from the extraction chamber by connecting the end cap to an open upper end of a collection vessel, said collection vessel including a collection plate at a base of the collection vessel; extracting the solvent gas by connecting a second egress fitting to the upper portion of the collection vessel connected by conduit to a second ingress fitting connected to the solvent tank and viewing the collection of the yield in the collection plate via a viewing vessel with an open lower end sealed at an angle to an upper portion of a sidewall of the collection vessel, the viewing vessel having an open upper end and an elongated viewing tube through the sidewall ending at a viewing port with a lens. The yield and other components may be heated via a heating element, aiding in removal of the gas while simultaneously viewing the yield in order to determine purity and viscosity of a desired yield.

DETAILED DESCRIPTION OF THE INVENTION

The inventors provide a unique closed loop organic material processing system to process organic materials to produce a clean product yield. The system enables both low volume and commercial volume material processing in a more ergonomic, economic, and safe manner. The present invention will be described in enabling detail using the following examples, which may describe more than one relevant embodiment falling within the scope of the present invention.

Figure 1:
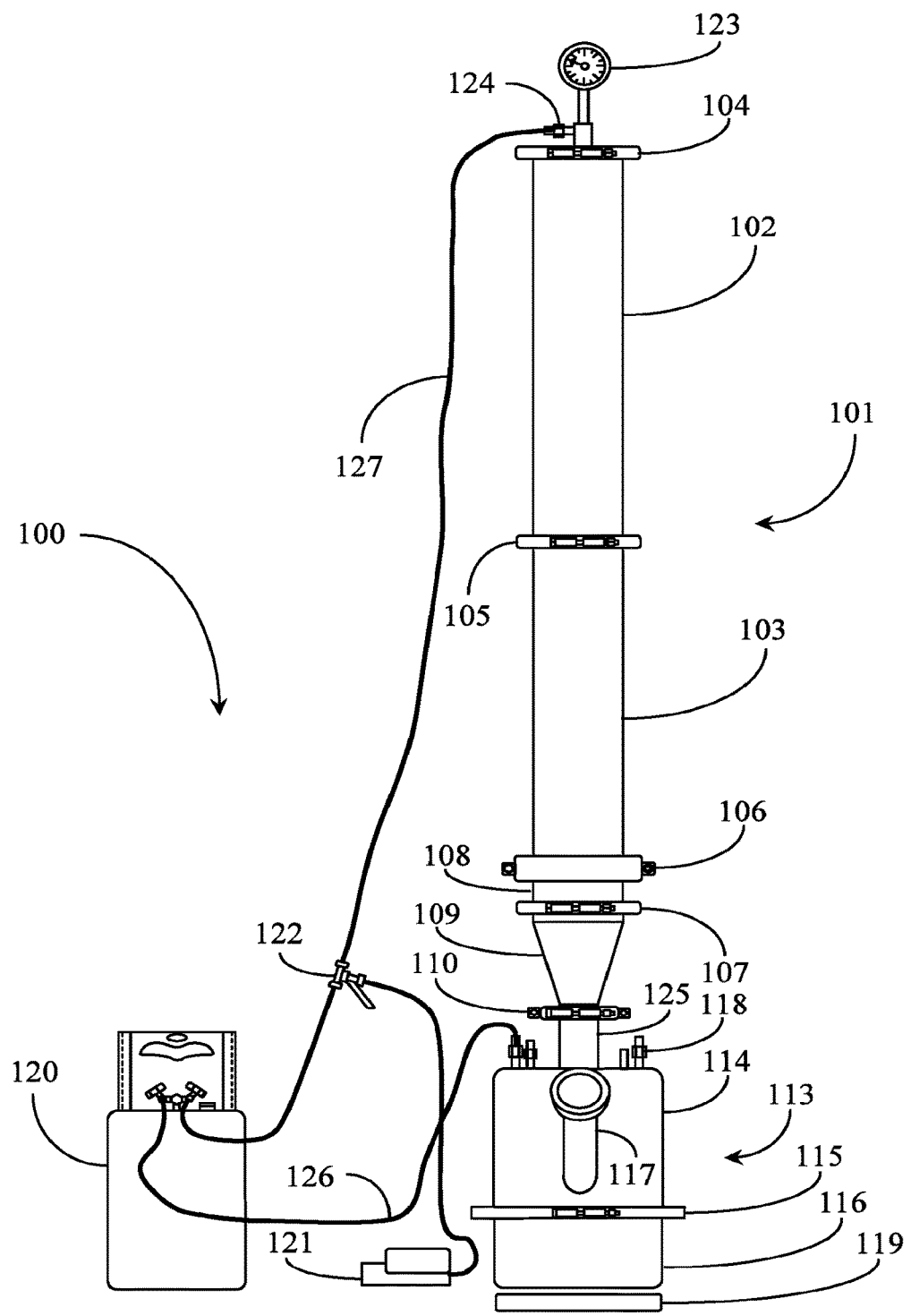
FIG. 1 is a front elevation view of an organic material processing system according to an embodiment of the present invention.

FIG. 1 is a front elevation view of an organic material processing system 100 according to an embodiment of the present invention. System 100, in one embodiment includes a modular container extractor assembly 101. Modular container extractor 101 is connected in close loop fashion to a recovery gas tank 120 and to a vacuum pump 121. Modular container extractor 101 includes at least one container shaped, in this embodiment as an elongate cylinder, in this case two cylinders 102 and 103. Containers 102 and 103 may be manufactured of stainless steel or another material that is durable and is resistant to potential contamination from solvents or gasses used to process materials. Gas may include butane gas, propane gas, or another gas in liquid or gaseous form.

Containers 102 and 103 are connected together by a pressure clamp and gasket assembly 105. Containers 102 and 103 have a common inside volume and an open inside diameter in this configuration comprising a material column for holding the material for processing. Container 102 is closed or capped at the upper end by an end cap clamp/gasket assembly 104, hereinafter referred to as end cap 104. End cap 104 has at least one fitting 124 for introduction and egress of a processing agent such as gas or a solvent. End cap 104 has a fitting for a vacuum gauge 123 adapted to display the vacuum reading inside extractor assembly 101. It is noted herein that there may be more than one gas fitting and vacuum fitting provided through end cap 104 without departing from the spirit and scope of the invention. The fittings shown are deemed sufficient however for describing the present invention. It is also noted herein that it is not necessary to have two containers in the stack configuration as one container may be removed leaving only a single container to process material.

Containers 102 and 103 have a nominal wall thickness that is suitable for holding a vacuum. Container 103 is seated in the configuration stack onto a clamp/gasket assembly 106. Extractor 101 further includes a relatively short tubular body 108 seated between clamp/gasket assembly 106 and a clamp gasket assembly 107. Tubular body 108 may be manufactured of stainless steel and may have the same or approximate inside diameter and outside diameter as containers 102 and 103. Tubular body 108 houses an annular filter plate (not illustrated). The filter plate may be affixed to or connected to tubular body 108 via welding in one implementation. In other implementations, the filter plate may be a separate part that is housed within tubular body 108 such as proximal to its lower end exhibiting a largely horizontal profile orthogonal to a center line of the tubular body.

Closed loop extractor 101 further includes a conical reducer tube 109. Reducer tube 109 may have a major outside diameter similar or identical to containers 102, 103, and tubular body 108 containing the filter plate. Reducer tube 109 may be manufactured of stainless steel and may have a major inside diameter similar or identical to the inside diameter of containers 102, 103, and tubular body 108 containing the filter plate. Reducer tube 109 is seated in this stack configuration between ring clamp gasket 107 and a ring clamp gasket 110. Reducer tube 109 may taper down or reduce the inside diameter from approximately 8 inches to 4 inches at a 2 to 1 ratio or another suitable ratio depending upon the diameters of the adjacent containers.

Modular container extractor 101 further includes a scope vessel assembly 113. Scope vessel assembly 113 may be connected to the reducer assembly at clamp gasket assembly 110. Scope vessel assembly 113 may be manufactured of a stainless steel and includes in this example, a top portion 114 and a bottom portion 116. Bottom portion 116 is adapted as a removable yield collection plate, pan, or bowl. Top portion 114 and bottom portion 116 of scope vessel 113 are connected together by a gasket clamp assembly 115. Top portion 114 of scope vessel 113 is closed at the upper end thereof with the exception of fittings such as fittings 118 and a central input or ingress tube 125. In one implementation, scope vessel 113 is fashioned using a robotic welding technique in order to reduce chance of vacuum and or gas leaks through broken welds. In one implementation scope vessel 113 may include a ball valve (not illustrated) that may be used to close off the scope vessel from the rest of extraction unit 101. One such scope vessel is described in more detail later in this specification.

Scope vessel 113 is adapted to receive processed and filtered product yield deposited on the bottom collection plate or pan 116. Scope vessel 113 may include at least two fittings 118. Fittings 118 may include a pressure release valve and at least one or more gas fittings. Scope vessel 113 may include at least one scope tube 117. In this example a gas line 126 connects fitting 118 to the recovery tank.

Scope tube 117 has a lens and is attached to the outer surface of the scope vessel at an angle so the an axis of scope tube 117 substantially intersects a center point of circular collection pan 116. This particular angled attachment enables a user to peer into the scope vessel, more particularly, at the entire bottom surface of collection pan 116 where the yield from processing is deposited. Scope tube 117 may be a stainless steel tube cut and welded at said angle to scope vessel upper portion 114. In one embodiment the welding is a robotic welding. Scope tube 117 is cut at the angle and welded to portion 114 of scope vessel 113 at a maximum angle of approximately 45 degrees or less of an angle for ergonomic, safety and optimal viewing purposes. The angle of attachment of scope tube 117 to vessel top portion 114 enables a user, typically a process operator, to more easily and safely view the volume of and consistency or viscosity of a product yield and to visually determine whether the gas and any other impurities have been fully recovered from the scope vessel and product yield after initial processing. The angled scope vessel has a length allowing the user to be physically separated from the system 100 while viewing creating a safer environment for the user while viewing. Scope length may be at least half the height of vessel assembly 113 or longer.

The viewing lens is at the top of scope tube 117 and may, in one embodiment, provide a magnified view that may be adjusted by turning the lens housing on a screw mechanism similar to a binocular lens. In one embodiment, scope vessel 113 includes a second port or window (not visible in this view) that includes a mounting interface for mounting a flashlight or other type of lighting to illuminate the inside of scope vessel 113, more particularly, at least the entire bottom surface area of the collection pan 116. In this view the second port and lighting are situated behind reducer tube 109 and scope vessel ingress tube 125. Scope vessel 113 may be heated during processing via a heating element 119 to help evacuate any gas or solvent from the scope vessel back into a recovery vessel or tank. It is noted herein that the use of heating may make it unnecessary in some embodiments to use a vacuum pump to evacuate gas, as the gas evacuates via temperature differentiation from the vessel 114 to tank 120 via line 126.

Extractor 101 may be loaded with organic material for processing through the top portion of container 102 in this implementation using two cylinder shaped containers. In one embodiment a user may connect more or less containers vertically, in stacked formation in order to dynamically adjust volume for processing a specific amount of material. Therefore, extractor 101 may be set up to process material using only one container such as container 103. In one implementation there may be more than two containers such as container 103 stacked to form extractor 101 without departing from the spirit and scope of the present invention.

Extraction unit 101 has connection line 126 to recovery tank 120 from one of scope vessel gas fittings 118 for the purpose of recovering the gas initially injected into the extraction unit and used to process or "wash" the organics loaded into the system. The recovery tank is used solely for collecting the gas from this processing. The gas recovered may be butane or propane gas or another gas that helps separate lipids from the organic materials being processed. Owing to the properties of such gasses where cold gas is dense and settles while heated gas rises and moves away from the heat source, one or more heating elements such as element 119 may be implemented to help recover all of the gas from extraction unit 101 after a process is deemed completed, whether a vacuum pump is also utilized or not.

Extraction unit 101 has a line connection 127 to recovery tank 120 from gas fitting 124 teed in at vacuum gauge 123. Vacuum pump 121 has a vacuum connection in line 127 leading from fitting 124 to recovery tank 120 at a vacuum valve 122 (installed in the line). This aids in collecting cooler gas left over in the materials higher up in the system. When a recovery gas tank is full it may be removed and replaced with another empty tank to recover more gas if necessary. Additional gas fittings allow for gas to be introduced into the system from an introduction source (not illustrated) while recovery tank is connected to the extraction unit. Generally speaking, a user may determine visually through scope 117 whether the yield in the collection pan 116, also termed a shatter platter by the inventors, is at the right amount of yield and at the right consistency or viscosity for harvesting.

In general use of the present invention a user may assemble extractor 101 leaving off the top end clamp for material loading purposes. A normal load for extractor 101 may be approximately a few pounds (5 pound or less) of organic materials. After the material is loaded the top is clamped on and a user may then check that all of the connections and fittings are secure. It is noted herein that larger diameter versions of the extractor may hold more material up to 15 pounds or more without departing from the spirit and scope of the present invention. Next a user may power on a vacuum pump like pump 121 to draw a vacuum within extractor unit 101. The vacuum may be just a slight or passive low pressure vacuum about 15 to 30 tor. A user may wait for a period of time about 15 minutes to see if the vacuum has held in the system. This is discernible at vacuum gauge 123 with the needle in the gauge remaining constant.

With a vacuum in place fresh gas may be injected into extractor 101 through though fitting 124. The line (127) may be disconnected from the recovery tank and reconnected to an introduction gas source or there may be two lines, one to recovery tank and one to introduction tank or can. Once connected to a fresh gas source, valve 122 may be opened to let gas into the extractor for processing. The typically cold gas washes through the material separating the useable lipids from the unusable organic matter. As the lipids are isolated or "extracted" from the organic materials they fall through the containers and a filter plate to keep organic contaminates which are larger than lipids out of the recovery tank. The filtered product falls through the reducer and down onto the center of the collection pan 116 along with residual gas. The gas introduction step may be repeated a number of times to effectively wash the product yield from the organic materials.

A user may check yield amount and consistency periodically or continuously by looking through scope 117. Once sufficient yield is detected a user may disconnect from an introduction gas source and then reconnect to recovery tank 120 for the purpose of recovering excess gasses or solvents from extractor 101, specifically vessel 114 so that the yield is cleaner. Recovery tank 120 has two valves, a red one indicating a liquid gas line and a blue one indicating a vapor gas line. By recovering all of the gas from closed loop extractor 101, the gas may later be used again or "recycled" back into the system. Moreover, the final product may be cleaner in terms of any leftover gas residuals.

After recovering gas from extractor 101 into recovery tank 120 the valves on the tank may be closed and the recovery tank disconnected. The collection pan 116 may then be removed from scope vessel 113 for further processing or use.

Figure 2A:
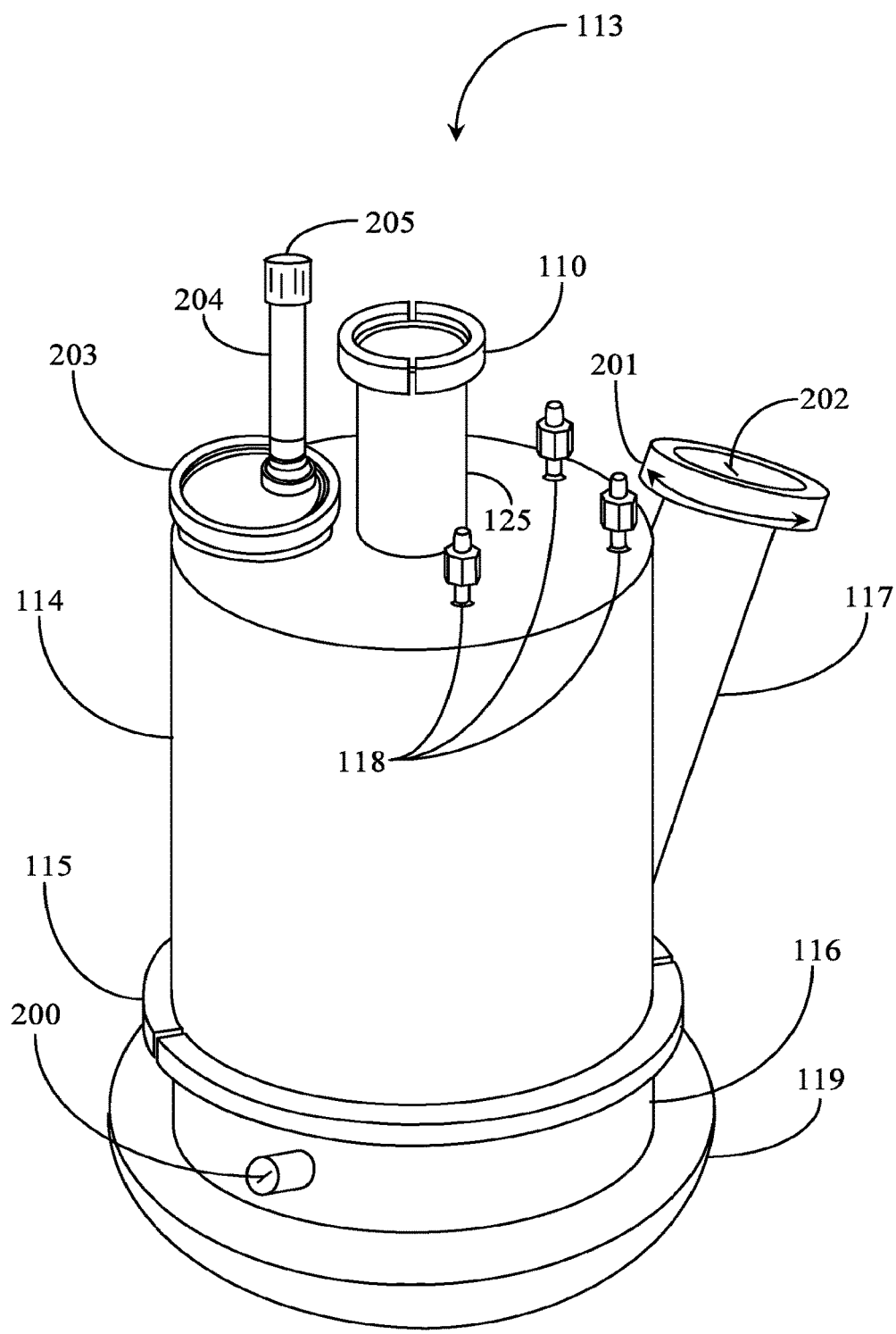
FIG. 2A is a perspective view of the scope vessel of FIG. 1.

FIG. 2A is a perspective view of scope vessel 113 of FIG. 1. Scope vessel 113 is a two-part assembly comprising top portion 114 and bottom portion 116 as previously described. In this example heating element 119 wraps about the bottom of collection plate 116. In a separate embodiment the heating element 119 may cover an exterior bottom surface of pan 116, either partially or completely, in order to provide a consistent and even introduction of heat to pan 116. A temperature gauge or thermocouple 200 is provided to be installed through the side of pan 116 to gauge the temperature within the scope vessel. In this way a user may see what temperature exists within the collection pan 116 or the collected product in pan 116 of scope vessel 113 at will. Clamps 115 and 110 are depicted without hardware in this example for clarity. A heater increases the temperature of the yield which causes evacuation of left over gas in the product, if any. It is noted herein that a vacuum may be first drawn on an empty recovery tank before gas may be further evacuated from the scope vessel. Heat at the scope vessel and vacuum in the recovery tank simultaneously enables more efficient gas recovery.

Scope tube 117 has a top piece or lens housing 201 that holds or contains a lens 202 to enable enhanced viewing of the product yield collected in pan 116. In one embodiment lens 202 may be a magnifying lens enabling viewing of the entire surface of the product within pan 116 or a more magnified view of the product in pan 116. The lens 202 may be brought into focus by rotating housing 201 bi-directionally over a screw mechanism according to the double arrow. In one embodiment tube 117 may be extendable outward and retracted inward according to a specific focus distance. In still another embodiment, an illumination source such as one or more light emitting diodes may be housed within scope tube 117 or in housing 201 in a manner not obstructing the lens to create more back lighting for viewing the yield.

In this example scope vessel 113 includes a second port or window 203 that supports mounting of a flashlight 204 with an off/on switch 205. A user may power on flashlight 204 via switch 205 to illuminate the entire interior surface of collection pan 116. In one embodiment the inside surface of pan 116, and in one embodiment, tube 117 is highly polished to a mirror or near mirror finish providing excellent light and image reflection to aid in illuminating the entire bottom area of the pan containing the yield. In one embodiment, lens housing 201 and lens 202 are removable such that lens 202 may be replaced with another lens.

In one embodiment lenses may include those having different colors for visually enhancing or improving the view of the yield. For example, using a color that provides a view having more contrast. Moreover, lighting color choices in both conventional flash light bulb or LEDs may be utilized to enhance or improve lighting for viewing. In a further embodiment the optical view port comprising tube 117 housing 201, and lens 202 may be adapted for an optic capture housing and cable that may capture images or a live cam feed of the yield as it is deposited and forward them to a remote computing appliance such as a lap top computer or a smart phone. It is noted herein that if there is a light source at the lens housing on scope tube 117, an additional port and flashlight are not required to practice the present invention. Having the light source or sources confined to the scope tube/lens housing eliminates the need for another port and flashlight reducing potential leak points in the vessel and simplifying its construction.

Figure 2B:
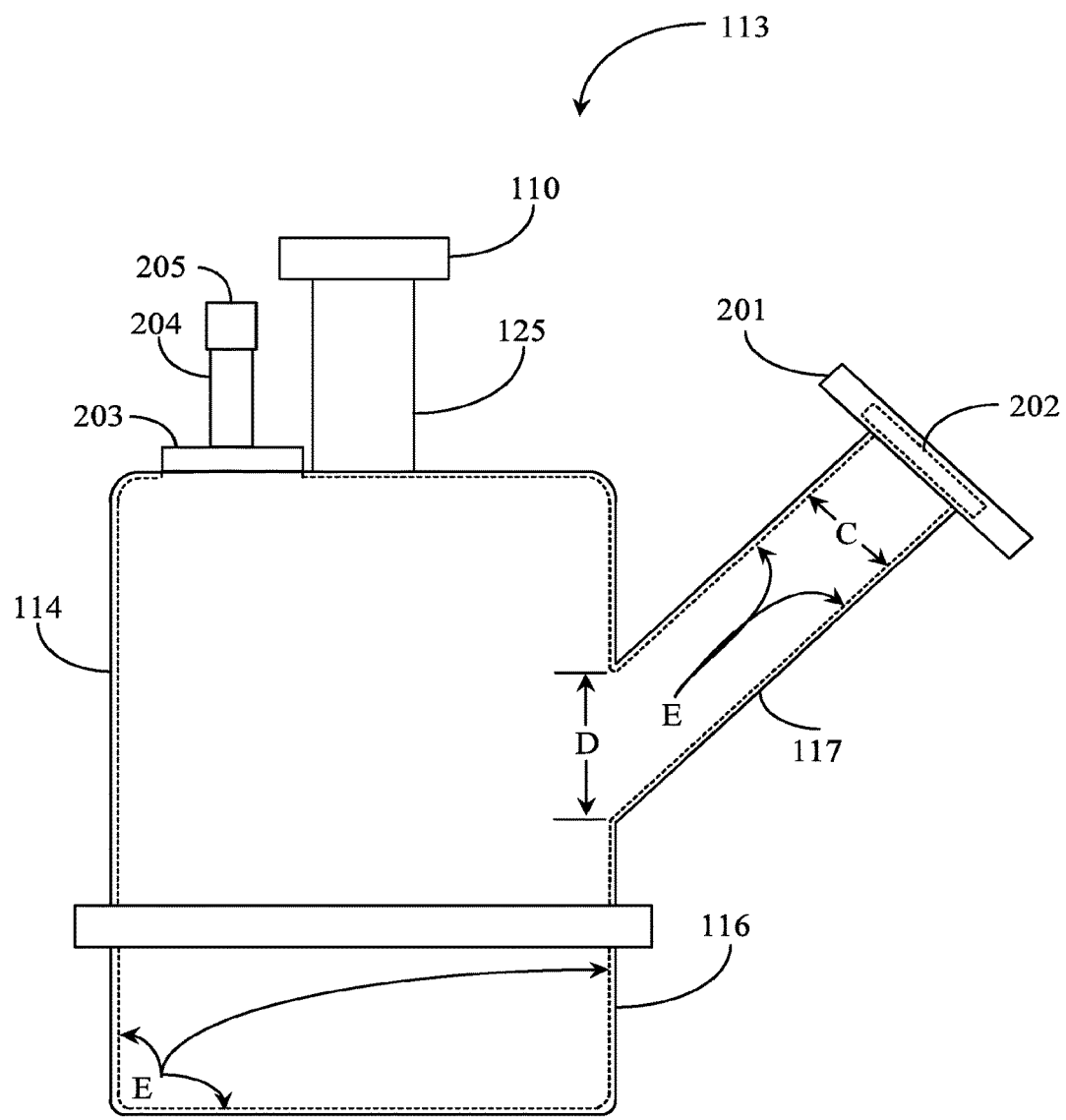
FIG. 2B is a plan view of the scope vessel of FIG. 1.

FIG. 2B is a plan view of scope vessel 113 of FIG. 1 depicting polished surfaces and angle for viewing yield according to an embodiment of the present invention. Vessel 113 includes elements that were introduced further above with respect to FIG. 2A. Some elements depicted herein are not reintroduced though the element numbers representing those elements may be included herein.

Scope tube 117 is welded into top portion 114 of vessel 113 at approximately a 45-degree angle, or less. The actual angle may vary somewhat without departing from the spirit and scope of the invention. In this example, the inside surfaces of tube 117 and pan 116 have a reflective "mirror" finish E. Mirror finish E enables all of the surface area to reflect light and images. Light source 204 provides illumination in this example, however other light sources may be substituted there for without departing from the spirit and scope of the invention such as LEDs discussed further above.

Scope tube 117 has an inside diameter C. A diameter D represents the diameter of the weld interface or passage from the tube 117 into the scope vessel 113. Due to the angled attachment of tube 117 to top portion 114, diameter D is significantly larger than diameter C providing more room to view the yield in pan 116. In combination, mirror surfaces E and larger diameter D of tube 117 enable a viewer to see the whole bottom area of pan 116.

Figure 3:
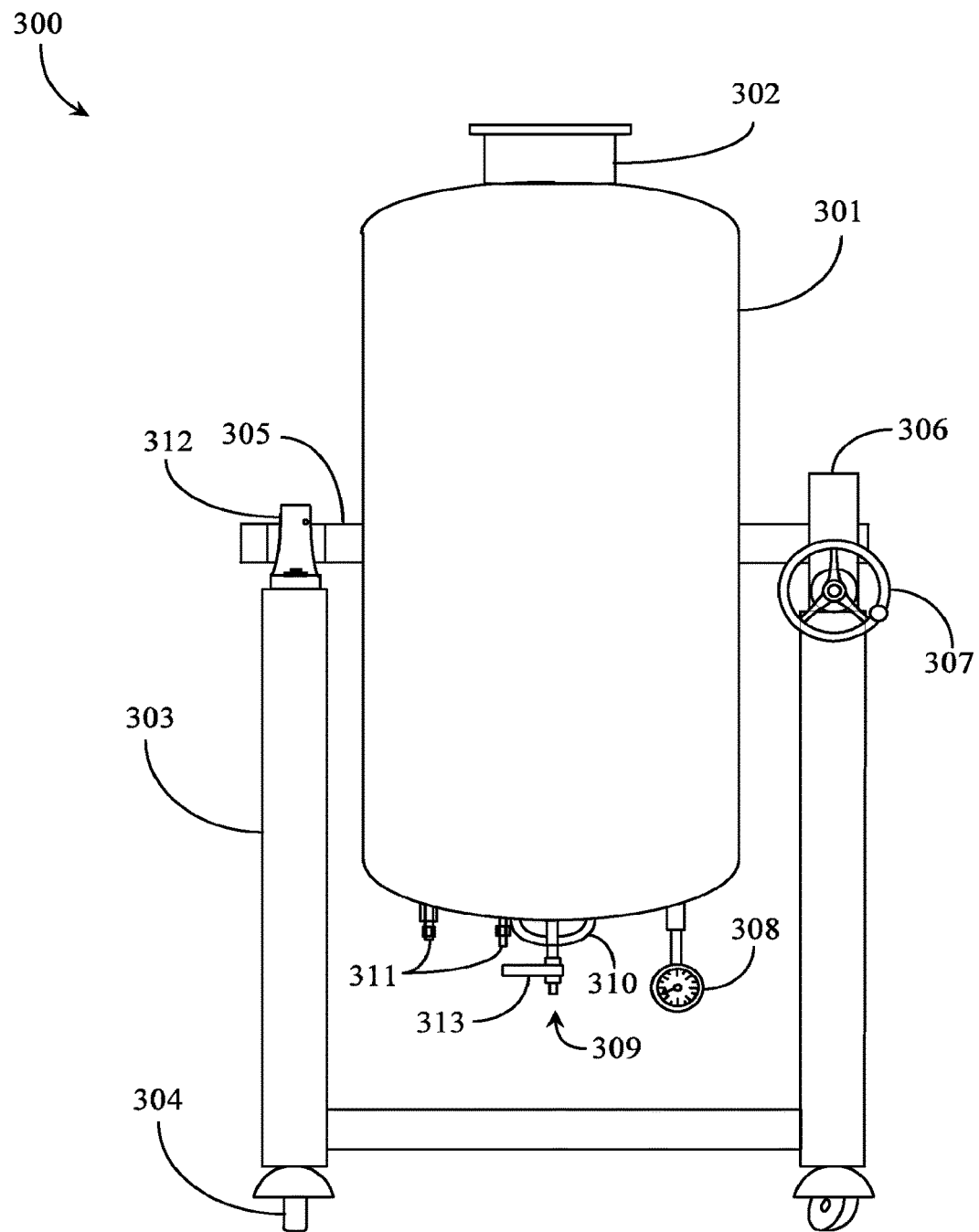
FIG. 3 is a front elevation view of a commercial grade organic material processing system according to an embodiment of the present invention.

FIG. 3 is a front elevation view of a commercial grade organic material processing system 300 according to an embodiment of the present invention. Processing system 300 may be referred to hereinafter as a commercial extraction unit or extractor 300. Extraction unit 300 includes a commercial grade chamber 301 for holding a much larger amount of organic materials for processing than, for example, containers 102 and 103 of the embodiment shown in FIG. 1. Chamber 301 may be fabricated from stainless steel tubing. Chamber 301 includes an opening central to one end and a flanged collar 302 for connecting to a larger commercial version of a filter plate and a reduction tube assembly similar in function to apparatus 108 and 109 of FIG. 1. A commercial grade scope vessel (not illustrated) would be connected to the aforementioned assembly to form the stack configuration. The mentioned components whose counterparts are depicted in FIG. 1 are left out of this view for clarity.

Chamber 301 is fixedly mounted at a balanced center point along the length of the chamber to an axle 305. Axle 305 may be fabricated of stainless steel or another durable metal. Axle 305 is supported by an axle bearing housing 312 on one side of chamber 300 and by a drive gear housing 306 at the other end of chamber 300. In this example, axle bearing housing 312 and gear housing 306 are supported by a mobile frame structure 303. Frame 306 may be fabricated from any durable metal or material capable of supporting the weight of chamber 301 loaded with material. Axle 305 is rotatable via a turn wheel 307 connected to a drive shaft, in turn connected to a gear assembly within gear housing 306. Axle 305 rotates in a bidirectional manner at the turn of turn wheel 307.

Chamber 301 includes fittings 311. Fittings 311 may include one or more gas fittings, at least one vacuum fitting and a pressure release fitting. Chamber 301 includes a centrally disposed spider valve assembly 309. Spider valve 309 comprises four gas inlet passage ways 310 that intersect at an inlet tube with a sphere or ball valve and handle. Spider valve 309 is adapted to increase the intake force and amount of fresh gas injected into the extraction chamber. Chamber 301 is adapted to accept a vacuum and includes a vacuum gauge 308 to enable an operator to discern the vacuum within the chamber and to see if it holds (no vacuum leak). Frame structure 303 includes wheels 304 of which there are four, two in front and two (not visible) at the rear of the structure as will be detailed further later in this specification.

Chamber 301 may be loaded with material through an opening at the end opposite spider valve 309, hidden in this view by collar 302. The opening may have a screw on cap or lid with a gasket that is vacuum proof once installed. An operator may crank turn wheel 307 in any direction to spin chamber 301 about axle 305. This may be performed after materials are loaded into chamber 301 and initial gas infusion through spider valve 309 for the purpose of gaining maximum exposure relative to gas and the loaded organic materials. The chamber may then be connected to a filter plate/reducer assembly and a scope vessel to collect the product extracted from the organic materials. It is noted herein that the scope vessel ingress tube may include a ball valve to isolate the scope vessel from the material containers.

Extraction system 300 may be connected to a recovery tank and vacuum pump as depicted in FIG. 1 above with system 101. In one embodiment, a ball valve may be connected between the reducer tube and the inlet tube of the scope vessel that may remain closed until a secure connection to the scope vessel has been accomplished. The valve may be opened to enable the yield to be deposited in the collection pan as was described relative to the process in FIG. 1.

Figure 4:
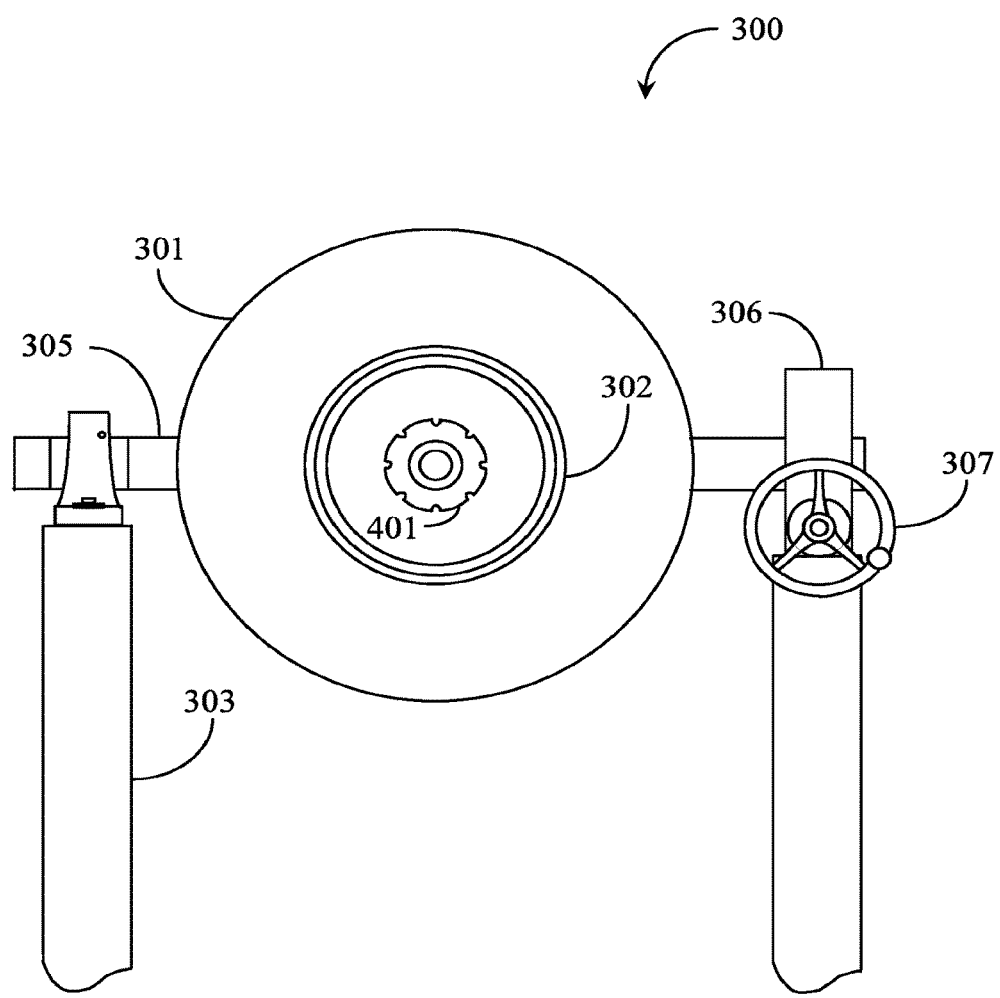
FIG. 4 is a rotated view of the material processing system of FIG. 3.

FIG. 4 is a rotated view of material processing system 300 of FIG. 3. In this view, chamber 301 is rotated 90 degrees toward the viewer to depict a screw on cap and gasket 401 covering the opening in the chamber, through which organic materials are loaded for processing. Collar 302 may be connected to a filter plate tube similar to tube 108 of FIG. 1 via a clamp gasket assembly and then to a reducer tube similar to reducer 109 and then to the scope vessel inlet tube.

Rotation of chamber 301 ninety degrees further presents the material load end of the chamber in a downward and vertical position for interfacing with the aforementioned components to enable yield collection. It is noted herein that the dimensioning of the reducer tube component relative to interfacing openings may be different than those dimensions for the extractor of FIG. 1 owing to different dimensions of the tubes between the split tube and the rotating extractor units. A user may operate turn handle 307 several times to spin chamber 301 about axle 305 with the aid of gear housing 306 enabling dispersal of gas throughout the organic material loaded into chamber 301 to maximize exposure of the material to the gas. This approach maximizes yield while conserving gas. Gas is recovered in the same way as described previously with extractor 101 of FIG. 1.

Figure 5:
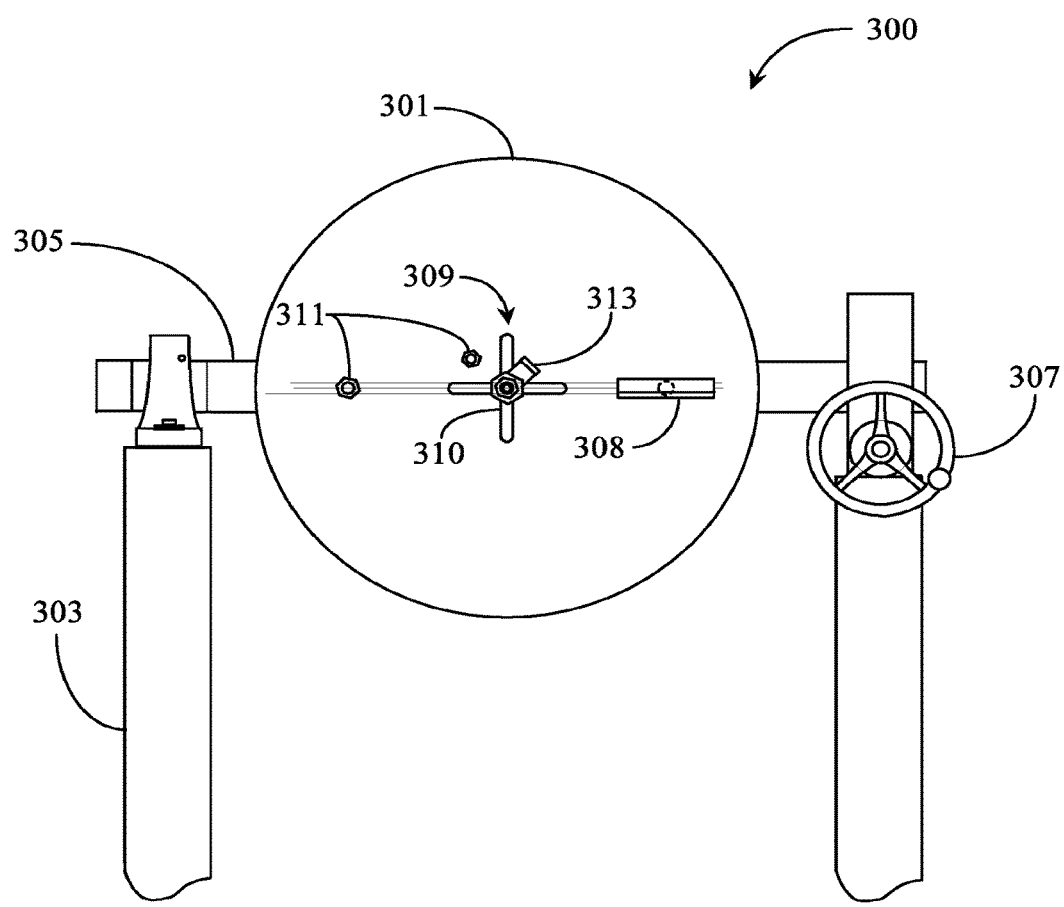
FIG. 5 is a rotated view of the material processing system of FIG. 3.

FIG. 5 is a rotated view of material processing system 300 of FIG. 3. Extraction system 300 depicts fittings including one or more gas fittings, at least one vacuum fitting and a pressure release fitting. Spider valve assembly 309 includes at least four gas inlet passages 310, and a valve handle 313 for opening and closing the valve and access to the passageways 310. Spider valve 309 is adapted to increase the intake force and amount of fresh gas injected into the extraction chamber as previously described.

Figure 6:
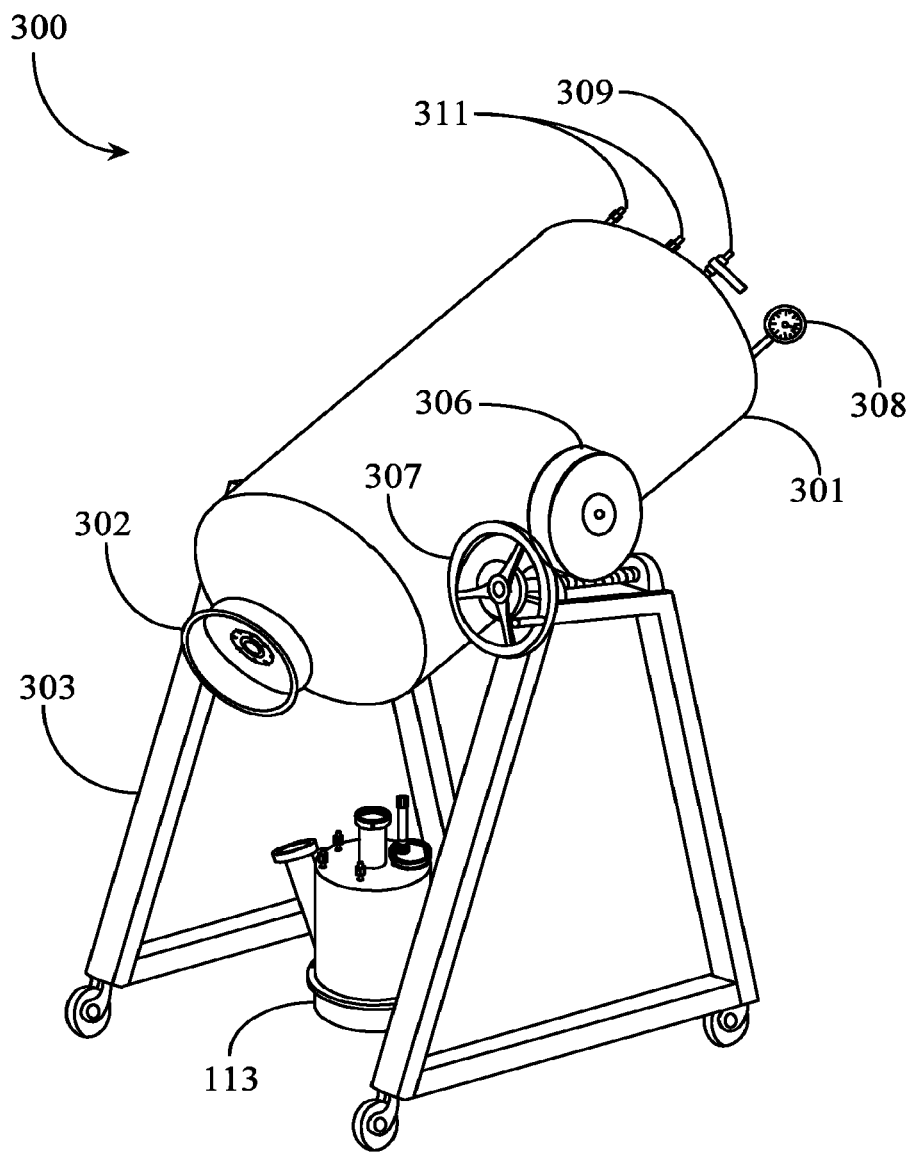
FIG. 6 is a perspective view of the commercial grade organic material processing system of FIG. 3 with the scope vessel of FIG. 2.

FIG. 6 is a perspective view of the commercial grade organic material processing system of FIG. 3 with the scope vessel of FIG. 2. Extraction system 300 is depicted in perspective view to show frame 303, which is on wheels that may include individual wheel brakes (not illustrated). Chamber 301 may be rotated to a vertical position using turn handle 307 with collar 302 facing downward to interface with a reducer component (not illustrated) that in turn is connected to the inlet tube of scope vessel 113. It is noted herein that in one implementation a scope vessel may have altered dimensioning relative to interface opening (inlet tube) and overall capacity of the chamber for interfacing with extraction system 300 without departing from the spirit and scope of the present invention.

Figure 7:
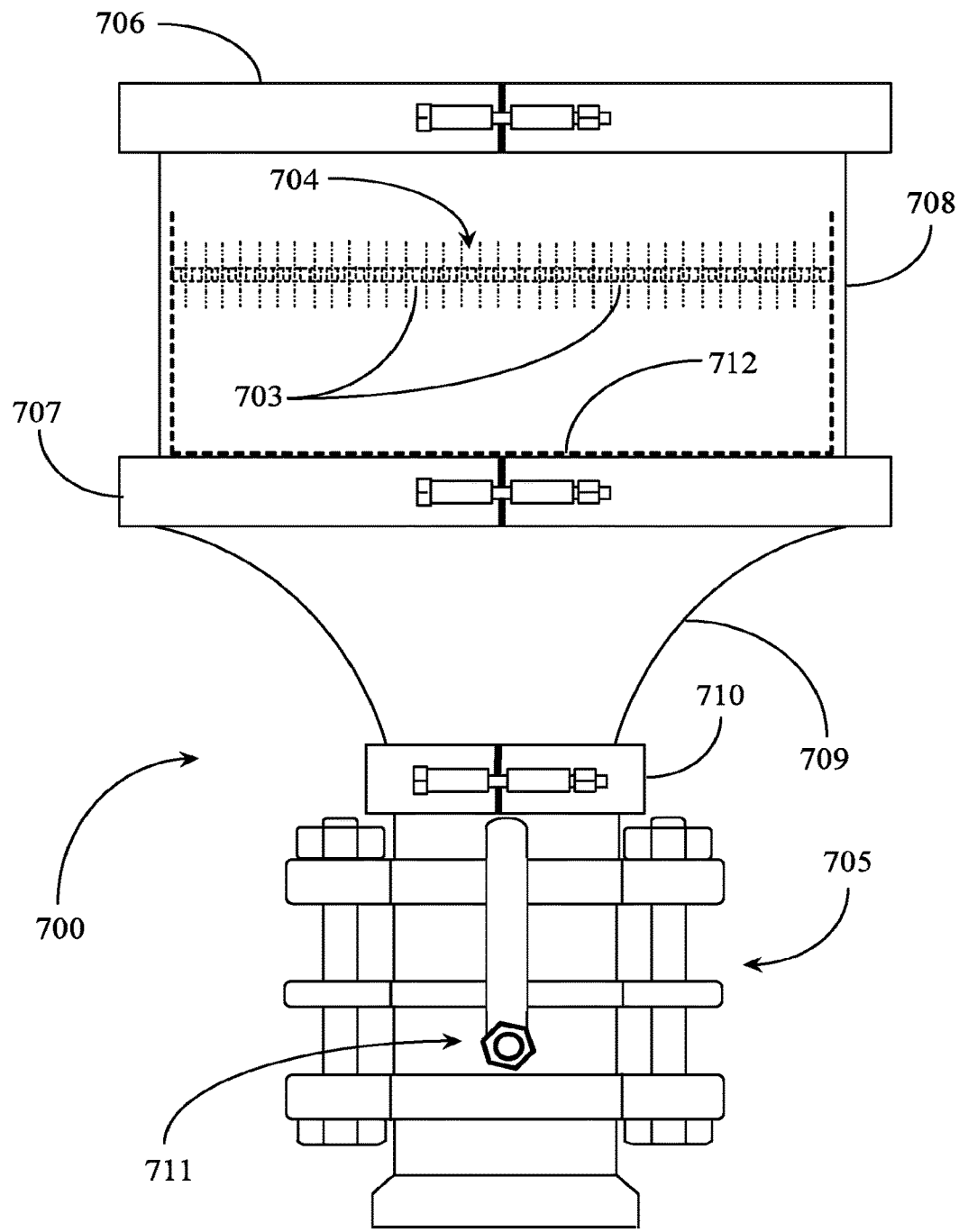
FIG. 7 is a front elevation view of a reducer assembly according to an embodiment of the present invention.

FIG. 7 is a front elevation view of a reducer assembly 700 according to an embodiment of the present invention. Reducer assembly 700 is analogous in one respect to the reduction components 108 and 109 depicted in FIG. 1 except that reducer assembly 700 includes a sphere or "ball" valve and handle 711. In this implementation reducer assembly 700 includes a filter plate tube 708 seated between a clamp gasket assembly 706 and a clamp gasket assembly 707. Filter plate tube 708 houses a filter plate 704, which may be an annular plate or baffle that occupies the entire diameter within the plate tube 708 and presents orthogonally from the material chamber center line. Filter plate 704 includes multiple small openings 703 on the order of microns for allowing yield product (lipids) to pass through preventing larger material particulates from entering reduction tube 709.

Filter plate 704 may be set more toward the bottom of tube 708 without departing from the spirit and scope of the present invention. The present depiction is logical only. Filter plate 704 may be manufactured of stainless steel or other materials that may be suitable for a baffle plate that are resistive to contamination from solvents used in the processing. Filter tube 708 may also include an industrial particulate filter such as a filter 712 that has further reduced openings in the micron scale for enabling lipids to pass but preventing non-desired organic residues from passing through, the filter openings of approximately 0.5 to 5.0 micron size. Filter 712 is logically represented herein. Filter 712 may be manufactured of a nylon or other suitable fabric and may be replaced periodically with a new filter between processing batches of material.

In this implementation a sphere valve tubular body 705 is added that is connected to reduction tube 709 by a clamp gasket assembly 710. Body 705 houses sphere valve and handle assembly 711. The lower end of valve 711 is flared to accept interface with the inlet tube 125 of FIG. 2B, for example, of a scope vessel 113, while clamp 706 may engage collar 302 of FIG. 4. The reduction components for both extraction systems filter out undesired organic particulates while enabling lipids to pass through and wherein those lipids are directed toward the top center of the scope vessel where they may fall onto the center of the removable collection pan 116 of FIG. 1. The exact size of the openings in filter 712 and in baffle or filter plate 704 may be varied in size according to goals established in processing relative to lipid purity of the final yielded product.

Figure 8:
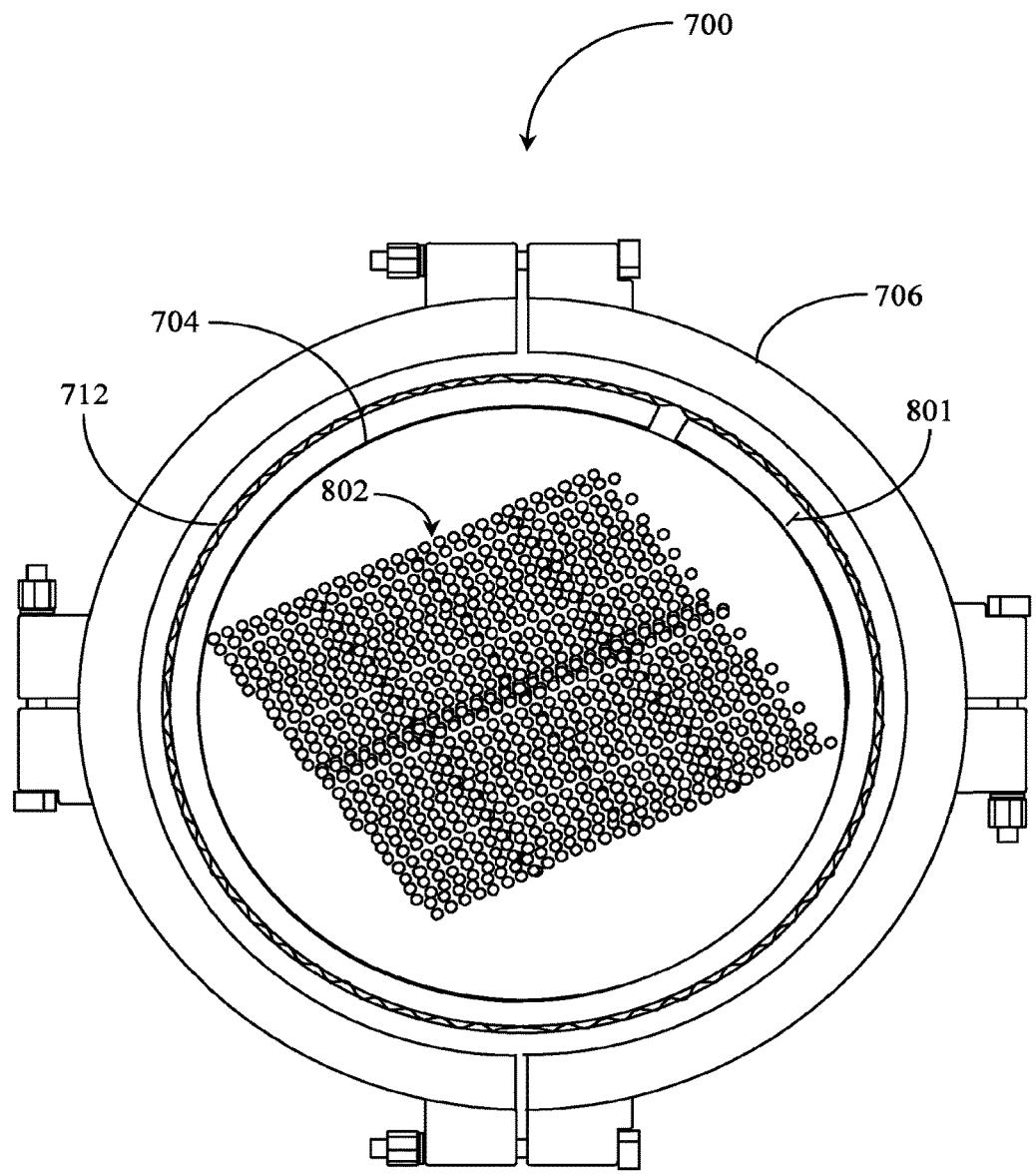
FIG. 8 is a top view of the reducer assembly of FIG. 7.

FIG. 8 is a top view of reducer assembly 700 of FIG. 7. Reducer assembly 700 includes a retainer ring 801 that sits over filter plate 704 and functions to retain filter 712 in position by virtue of spring force so that there are no gaps to enable pass-through of undesired organic particulates. Specific number of and sizes of the openings through the filter plate may be a matter of preference with multiple filter plates of different opening number and size being available to an operator. Similarly, the filter (nylon) 712 may also come in a variety of opening size specifications, typically measured in microns.

Figure 9:
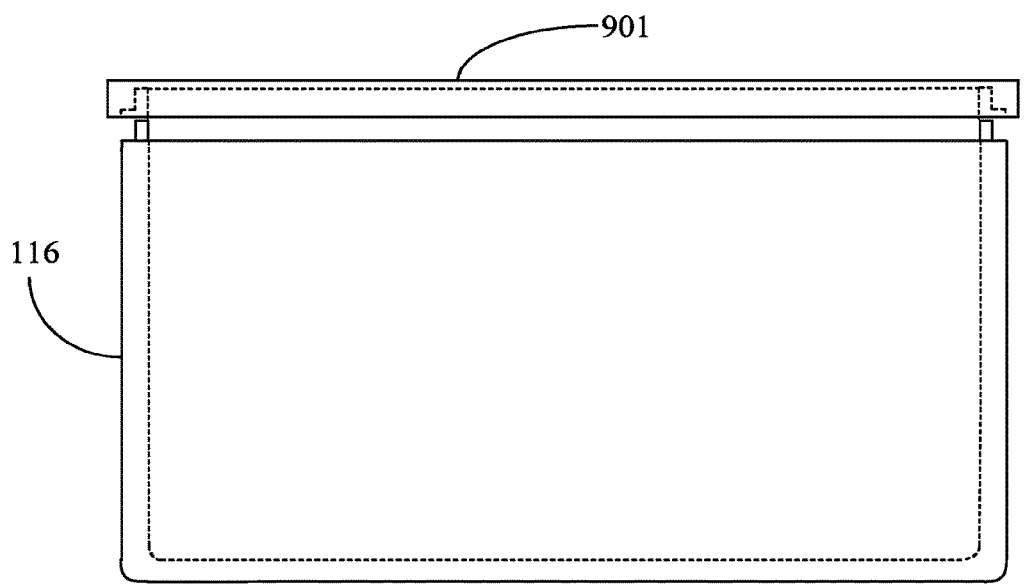
FIG. 9 is an elevation view of a collection pan according to an embodiment of the present invention.

FIG. 9 is an elevation view of collection pan 116 according to an embodiment of the present invention. Collection pan 116 comprises the bottom portion of a scope vessel and is where yield is collected during and after processing is complete. In this example, collection pan 116 includes an add-on screw on lid and gasket to cover uncollected yield to prevent contaminants such as dust, hair, etc. from interacting with the process yield after harvested from the device. In one implementation, lid 901 is a stainless steel lid that an operator may screw onto a threaded rim on collection pan 116. The stainless steel lid may incorporate means for venting gas further extracted from the product with an oven manufactured for such processes after initial collection. In another embodiment, lid 901 may be a plastic component that screws onto collection pan 116 or that may be snugly pressed onto the rim of the pan similar to a Tupperware™ lid.

Figure 10:
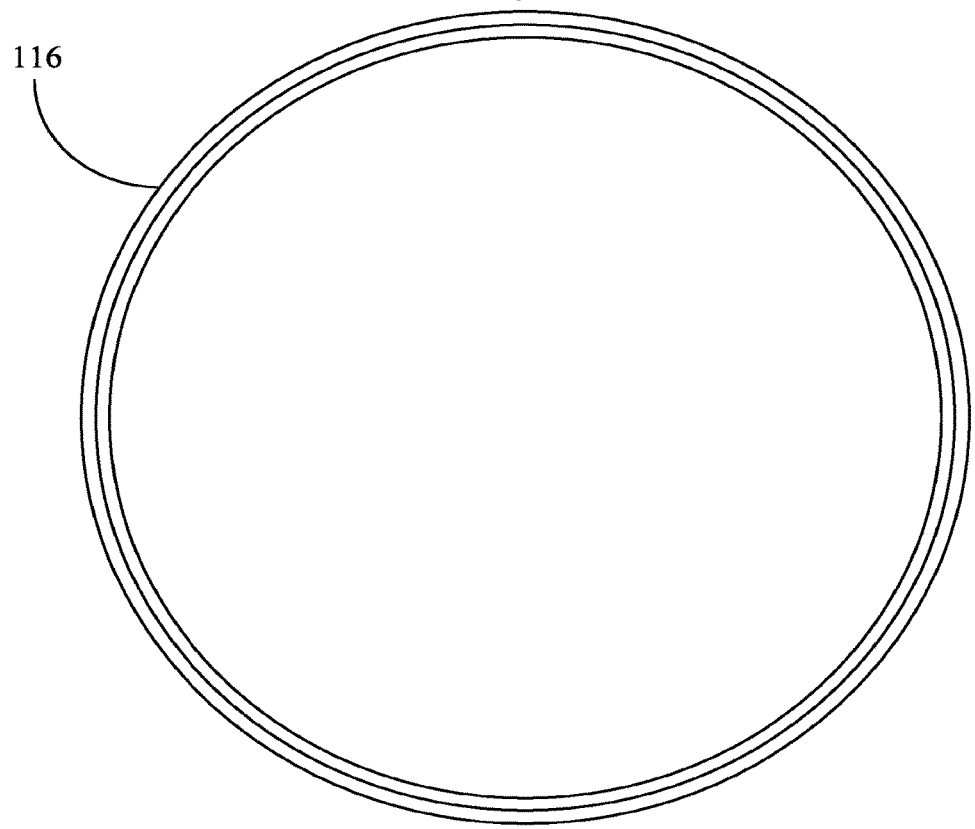
FIG. 10 is a top view of the collection pan of FIG. 9.

FIG. 10 is a top view of collection pan 116 of FIG. 9. Collection pan 116 is annular and may vary in diameter according to scope vessels of differing diameters. The depth dimension of pan 116 may also vary by design. In a preferred embodiment the center area of the pan is where all of the yield is deposited due to funneling of the yield through the reduction and filter components just above the inlet of the scope vessel. In one implementation one or more thermocouples (not illustrated) such as thermocouple 200 of FIG. 2 may be provided to ascertain temperature within the collection pan, such as when the pan is heated using a heating element similar to heating element 119 of FIG. 1.

Figure 11:
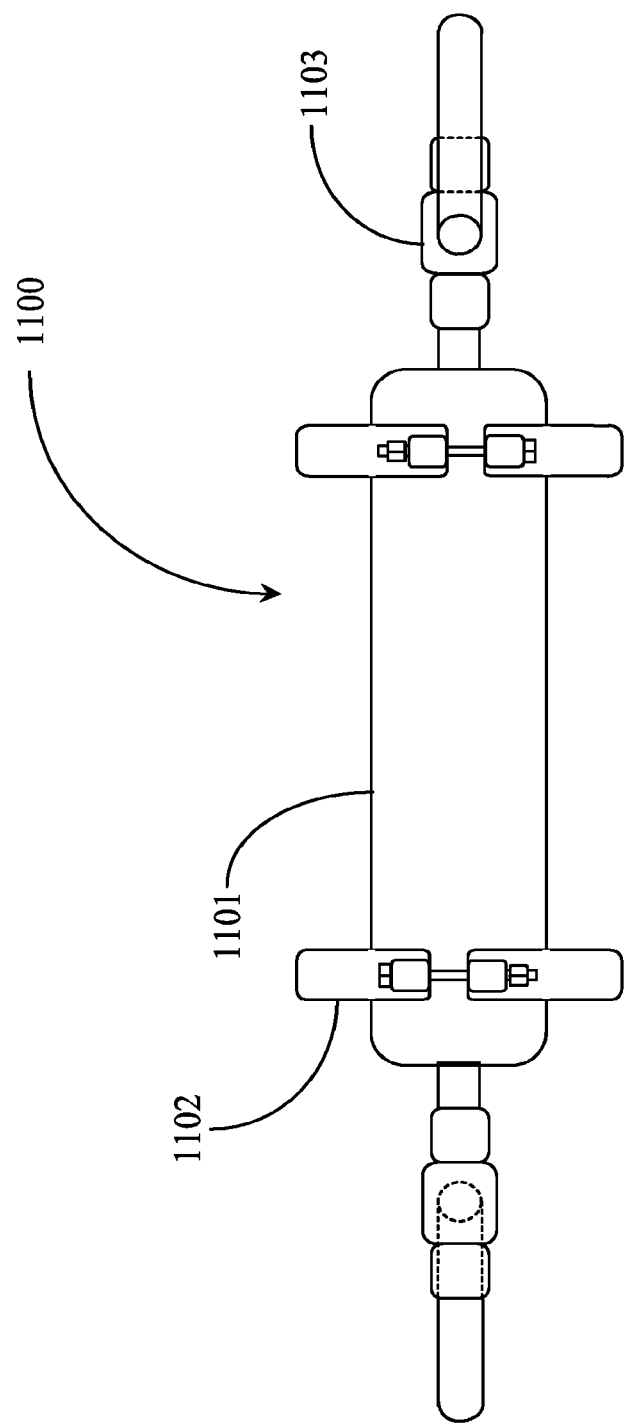
FIG. 11 is an elevation view of a desiccation chamber according to an embodiment of the present invention.

FIG. 11 is an elevation view of desiccation chamber 1100 according to an embodiment of the present invention. In one embodiment of the present invention a desiccation chamber may be provided to dry up any moisture present in a gas recovery line. Desiccation chamber 1100 may be connected inline between a scope vessel and a recover gas tank. Desiccation chamber 1100 comprises a hollow tubular body 1101 connected to end caps 1104 at each end by clamp gaskets 1102. Desiccation chamber 100 may be manufactured of stainless steel or other suitable materials having high resistance to contamination. In this example sphere valves 1103 are connected at the ends of chamber 1100 so that inflow into the chamber and egress from the chamber to the gas recovery tank may be controlled such as to isolate the desiccant chamber for removal from the gas line.

In one embodiment an operator may remove clamp 1102 to access the inside of chamber 1100. A suitable desiccant material such as a dry silica gel or an anhydrous sodium hydroxide may be placed therein to trap moisture from passing gas during a gas recovery operation. Gas fittings at each end of desiccant chamber 1100 enable quick connection into the gas line from the extractor system (scope vessel) to the recovery tank.

In use of the present invention, an operator loads organic materials into a process container or chamber of an extraction unit or system like system 101 (modular container) or system 301 (commercial extractor). Once materials are loaded and the clamp gaskets or screw gasket (commercial extractor) are reinstalled, the operator may connect a fresh gas source to the system through one or more than one gas fitting. The operator may then connect a gas recovery tank to the extraction unit in a manner similar to that depicted in FIG. 1. The operator may draw a slight or passive vacuum on the extraction system using a vacuum pump similar to pump 121 connected to a gas recovery line at a valve such as valve 122.

An operator may monitor a vacuum gauge for a small period of time after drawing vacuum to determine if the vacuum state within the system is holding for subsequent processing. If the vacuum gauge indicates that a drawn vacuum is not holding, the operator may check clamps and connections involved for leaks or inaccurate installations. Once vacuum state is stable within an extraction unit for a set period of time, the operator may introduce gas from a fresh gas source into the extraction unit. The amount of and force of gas entering an extraction unit may vary between different units and according to materials processed, amounts of materials loaded, and overall yield goals.

After gas is introduced the "washing process" occurs as the gas interacts with the material to isolate the yield or lipids. In one embodiment vacuum may be drawn in a part of the system, for example in the upper container or material portion of the system but not the scope vessel and vis a vis (multiple container system). Vacuum may also be applied to the recovery tank and line up to the valve on the scope vessel. In the commercial grade extraction system (FIGS. 3-6), an operator may spin the chamber back and forth using the crank handle and drive gear assembly to maximize the "washing" of the organic material.

In the commercial grade system mentioned above the lid at the loading end is not replaced after loading so that the chamber may be subsequently connected to a reducer and filter plate assembly, instead implementing a sphere valve to close off the system for gas processing. In one embodiment recovered gas may be circulated back into the extraction unit one or more times after initial gas injection. In an alternative embodiment of the present invention a recovery gas tank such as tank 120 may contain an internal billow or inflatable device, to help create positive or negative pressure within the tank in order to drive gas back out of the recovery tank if recycled back into the system or into another collection tank or to draw gas back into the tank. In this embodiment, the inflatable device within the tank is connected to a fitting on the tank which is connected via to a pump, via a designated line. The pump capable of inflating or deflating the inflatable device, thereby adjusting the pressure within the tank.

Therefore, part of the process of moving gas to and from the system may involve alternate heating of different elements such as for example heating the scope vessel to help move gas back to the recovery tank and heating the recovery tank to move gas back into the system. In one embodiment this may be aided by vacuum draw as well.

In both types of extraction systems, the commonality in method is that the operator may visually monitor the scope vessel to view, under lighted conditions, the yield as it is deposited onto the bottom of the collection pan of the scope vessel. The angled (approximately 45 degrees, or less, from center line) and elongated scope tube such as tube 117 of FIG. 1 enables safe visual monitoring of the yield domain preventing accidental interaction with and possible injury by system components during the process. Additionally, the angle provides the ability to view the entire surface of the yield.

Once an operator is satisfied that processing is complete through visual monitoring including recovery of left over gas and, perhaps some time management, the operator may close off the system to the scope vessel and disconnect the vessel from gas lines and from the reduction tube. The bottom collection pan may then be removed containing the product yield, which may in turn be collected or harvested from the pan for use or for further processing to clean the yield from any leftover hydrocarbons from the gas residue. A machine designed for this purpose is detailed later in this specification.

Figure 12:
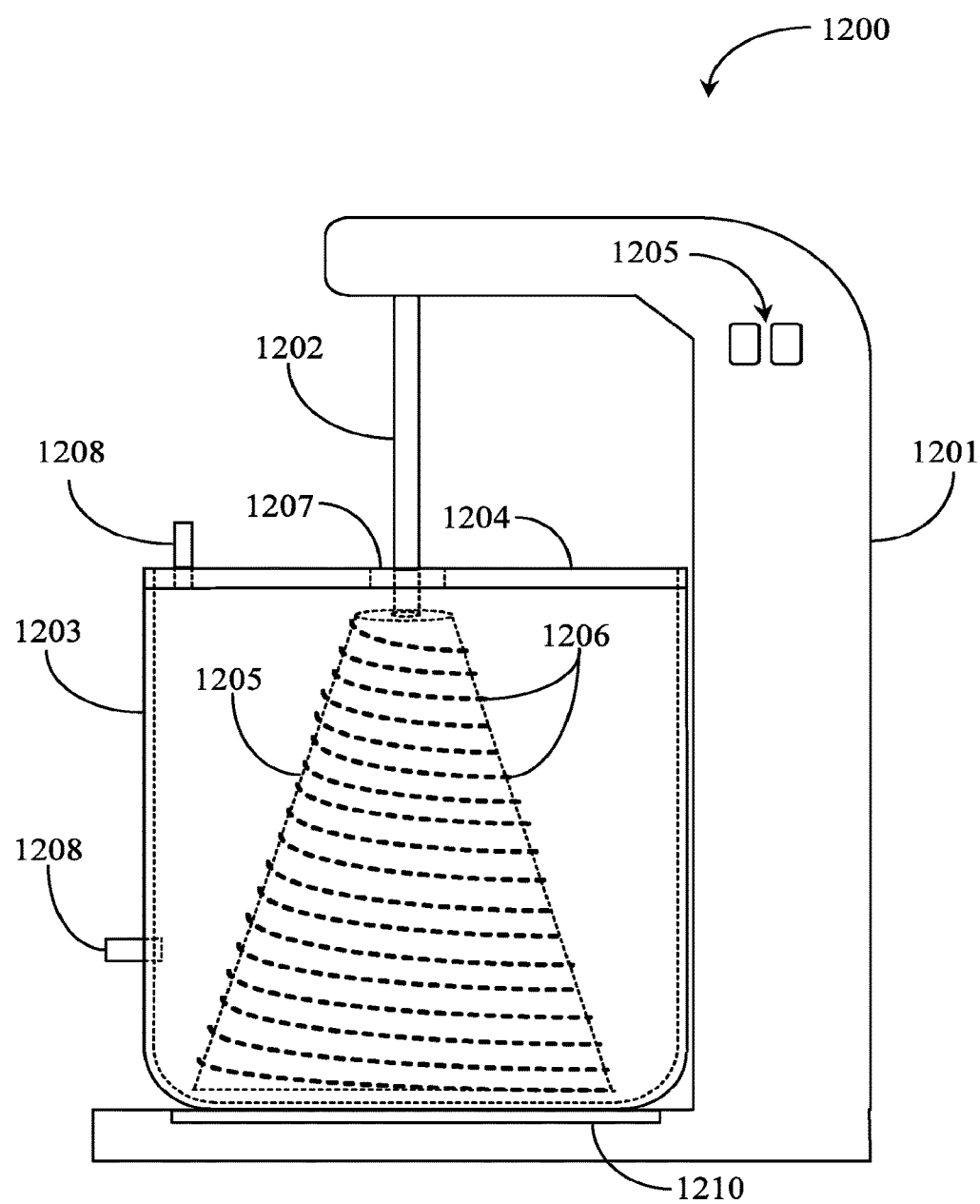
FIG. 12 is a side elevation view of a macerating machine according to another embodiment of the present invention.

FIG. 12 is a side elevation view of a macerating machine 1200 according to another embodiment of the present invention. Macerating machine 1200 may be electrically operated to macerate final product yield taken from plate 116 of system 100 or 300. The extraction process performed by machine 1200 is to further purify the yield by removing hydrocarbon contaminants that may be left over in the yield and to increase viscosity. Macerating machine 1200 includes a base and vertical housing 1201. Base and housing 1201 may be fabricated of a polymer that has a high heat resistance property. In one embodiment base and housing 1201 are cast metal or fabricated of stainless steel.

Housing 1201 may house an electric motor/gear assembly and plug wire (not illustrated) to operate a vertical spindle 1202. The base/housing portion 1201 of maceration unit 1200 may support an electric heating element or plate 1210 that may or may not include a thermocouple device (not illustrated). A chamber 1203 is provided to hold yield product for purification. Chamber 1203, in one embodiment, may be a rectangular or annular hollow stainless steel tube closed or capped at the bottom and open at the top to accept a screw or clamp-on lid 1204. Lid 1204 may utilize a gasket to affect a vacuum capable seal of the top part of the chamber. A vacuum-capable bearing 1207 may be utilized at a central portion of lid 1204 where spindle 1202 extends there through.

Spindle 1202 has connection in this implementation, to a conical device 1205 having a spiral flute 1206 wrapped thereabout spiraling upward and around the conical device 1205 to the top edge of the device. Conical device 1205 is suspended within chamber 1203 having a space between Housing 1201 includes electronic controls 1209 for powering on and off the motor driving the spindle. In one implementation controls 1209 include a power on/off switch, a spindle forward and reverse switch, and a variable speed switch. In one implementation heating element 1210 heats when power is supplied for driving the spindle in order to reduce viscosity of the product. In another implementation, controls 1209 further include a temperature control for setting a specific temperature or a set switch for low, medium, and high temperatures for the heating element.

Chamber 1203 may include one or more fittings 1208. Fittings 1208 may include one or more than one vacuum fitting, and one or more than one pressure release fitting without departing from the spirit and scope of the present invention. In use a final product yield may be placed into maceration chamber 1203 through the opening. Spindle 1202 may be inserted through vacuum bearing 1207 and connected to conical device 1205. Lid 1204 may then be screwed down or clamped down onto chamber 1203 sealing the product and conical device within. It is important to note herein that the conical device 1205 is always oriented vertically within wherein the wider base of the cone in facing downward.

An operator may then draw a vacuum on the chamber and may also initialize heating plate 1210. In one embodiment a vacuum gauge is provided to allow an operator to ascertain vacuum state within chamber 1203. The fluted edge 1206 of conical device 1205 spirals upward carrying the product yield upward under vacuum causing separation of hydrocarbons from the yield. The yield is carried upward and spins off of the conical device outward and falls back down, via gravity, to the bottom of the chamber.

Fluted edge 1206 may angle slightly upward from horizontal and may form an acute angle to the surface of conical device 1205. In one embodiment the flute is at a right angle to the surface of the conical device. In another embodiment the angle may be obtuse (greater than 90 degrees) with the surface angle of conical device 1205 while still maintaining a slightly upward angle from horizontal.

In one embodiment, flute 1206 is fabricated of a polymer and may be installed in parts to conical device 1205. In another embodiment, the flute is metal and is fabricated of one piece that may be installed onto the conical device by snapping into place or by standard mechanical methods. There are many possibilities.

Figure 13:
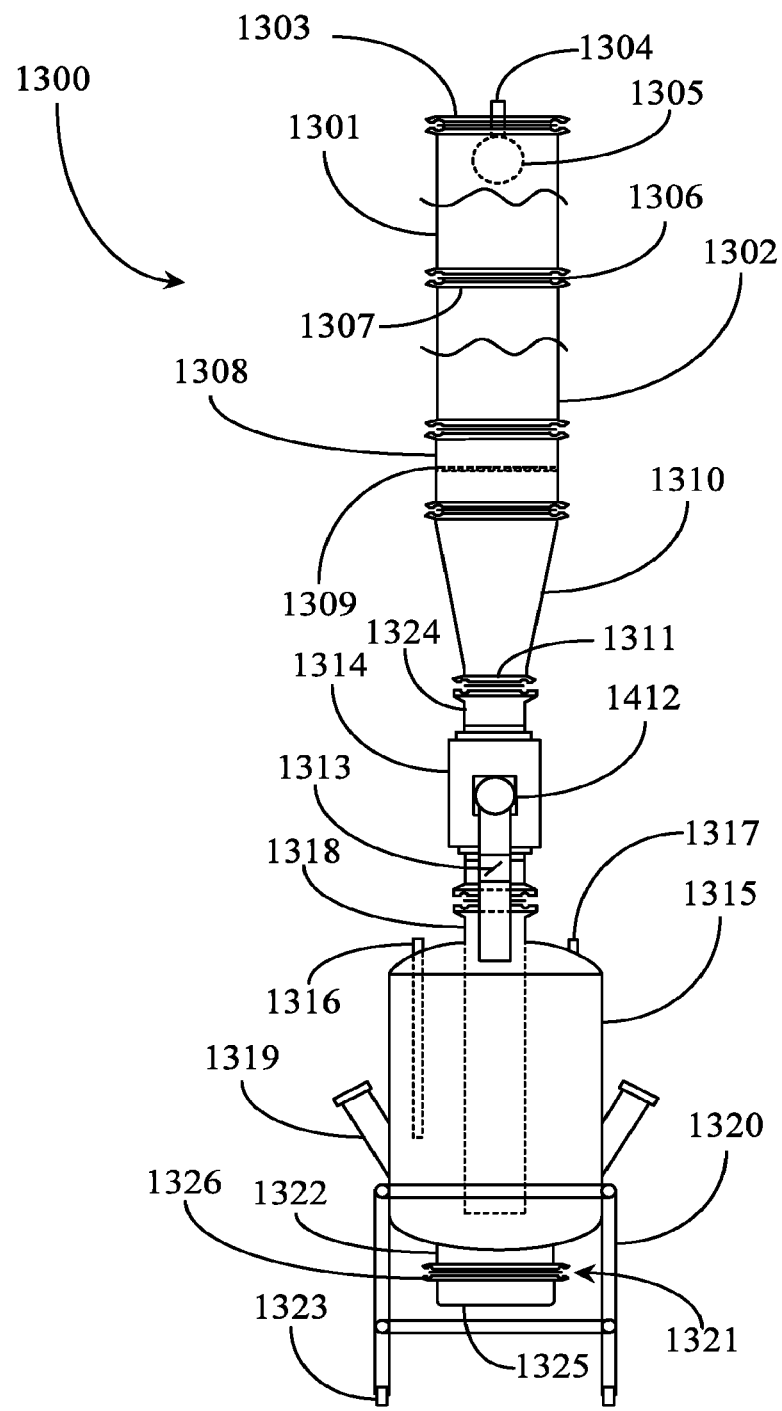
FIG. 13 is a front elevation view of an organic material processing system according to another embodiment of the invention.

FIG. 13 is a front elevation view of an organic material processing system 1300 according to another embodiment of the invention. Extraction system 1300 is a modified version of the modular container system depicted as extraction system 101 of FIG. 1. Extraction unit 1300 includes a series of connected containers such as container 1301 and container 1302, held together by clamp gasket assemblies such as clamps 1307 with gaskets 1306 situated there between. Containers 1301 and 1302 are depicted partially in this example (separation lines). In this implementation a shorter tube 1308 is provided that includes a filter plate 1309. The diameters of containers 1301, 1302 and tube 1308 are consistent for a unit but may vary according to different capacity units. For example, containers 1301, 1302, and tube 1308 may be 12-inch diameter, 8-inch or 6-inch, or any desired diameter depending upon volume of material to be processed without departing from the spirit and scope of the present invention. In one implementation smaller diameter containers may be inherently shorter than larger diameter tubes without departing from the spirit and scope of the invention. One or more containers may be used in this implementation without departing from the spirit and scope of the present invention.

Extractor unit 1300 includes a ball type spray valve connected to a male gas fitting 1304 provided through a closed clamp/gasket end cap 1303. When gas is introduced through fitting 1304. In one implementation a vacuum gauge (not illustrated) is also provided through the top clamp/gasket end cap. In one implementation spray valve 1305 is rotatable and may spin while gas is being introduced under pressure, for example with the tank including an inflatable device as described above. In one implementation spinning is passive and the force of introduced gas creates the spin in spray ball 1305.

In this implementation, extractor 1300 includes a reduction tube 1310 connected to tube 1308 via a clamp gasket assembly. The bottom end of reducer tube 1310 has connection to a sphere valve housing 1314 via a reduced diameter clamp gasket assembly 1311. Reduction diameter may be reduced from 12 to 4 inches or from 6 to 4 inches depending on the initial diameter. Other diameters and reduction diameters may be observed without departing from the spirit and scope of the invention. A sphere valve 1312 is contained within housing 1314 and may be controlled by valve handle 1313 for shutting off the valve and for opening the valve. Valve housing tube 1314 is in turn connected to an inlet tube 1318 on a scope vessel 1315 via a clamp gasket assembly 1324.

Also in this implementation, scope vessel 1315 includes two angled scope tubes 1319 in place of one scope tube such as tube 117 of FIG. 1. Scope tubes 1319 include all characteristics described on behalf of scope tube 117. In this implementation each scope tube 1319 includes a lens at the top extending away from the scope vessel with one or more lamps or LEDs positioned within the lens housing for illumination purposes. In one embodiment scope tubes 1319 are polished on the inside diameter surfaces to improve illumination by reflection. In one variation of this embodiment the polish is a mirror finished to reflect the light.

Scope vessel 1315 includes at least two fittings that may include gas fittings 1316 and 1317. In this implementation, the fittings have extension straws that extend downward and into the internal space of the vessel at least past mid-way. Scope vessel inlet tube 1318 also extends well within the interior of the scope vessel. The bottom portion of scope vessel 1315 opens into a collection pan 1321 comprising an upper portion 1322 and a lower portion 1325. Collection pan 1321 is held together relative to the two portions by a clamp/gasket assembly 1326. The bottom portion (1325) of pan 1321 is removable to take the product yield from the system. The modified design aids in concentrating the product yield into the center bottom of "platter" 1325. It is noted herein that there may also be a heating element and thermocouple associated with the bottom portion 1325 of the collection pan (not shown).

In this implementation extraction system 1300 is mounted atop a tubular frame structure 1320. Frame structure 1320 may be fabricated of stainless steel tubing. In other embodiments a rectangular steel tubing or steel sheet material may be used to construct the frame without departing from the spirit and scope of the present invention. In one implementation, frame 1320 includes four legs that have leveling screws 1323 at the bottom so that the yield may be kept at center of the bottom pan 1325. Extraction system 1300 may include one or more gas fittings and one or more vacuum fittings as described for earlier versions of the system.

In this system, material may be loaded through the top by removing end cap gasket assembly 1303. In operation, the system works like extractor unit 101 with regard to material loading, connection to vacuum pump and gas recovery tank, and connection to a fresh gas source for initial influx of gas to begin "washing" of the material. Elevating scope vessel 1315 off of the ground by use of frame 1320 provides easy and unfettered access to the product yield in collection pan bottom 1325. Spray ball valve 1305 includes multiple small openings to project inserted gas outward and downward evenly over the loaded organic material thereby reducing "wash time" for the loaded material.

Figure 14:
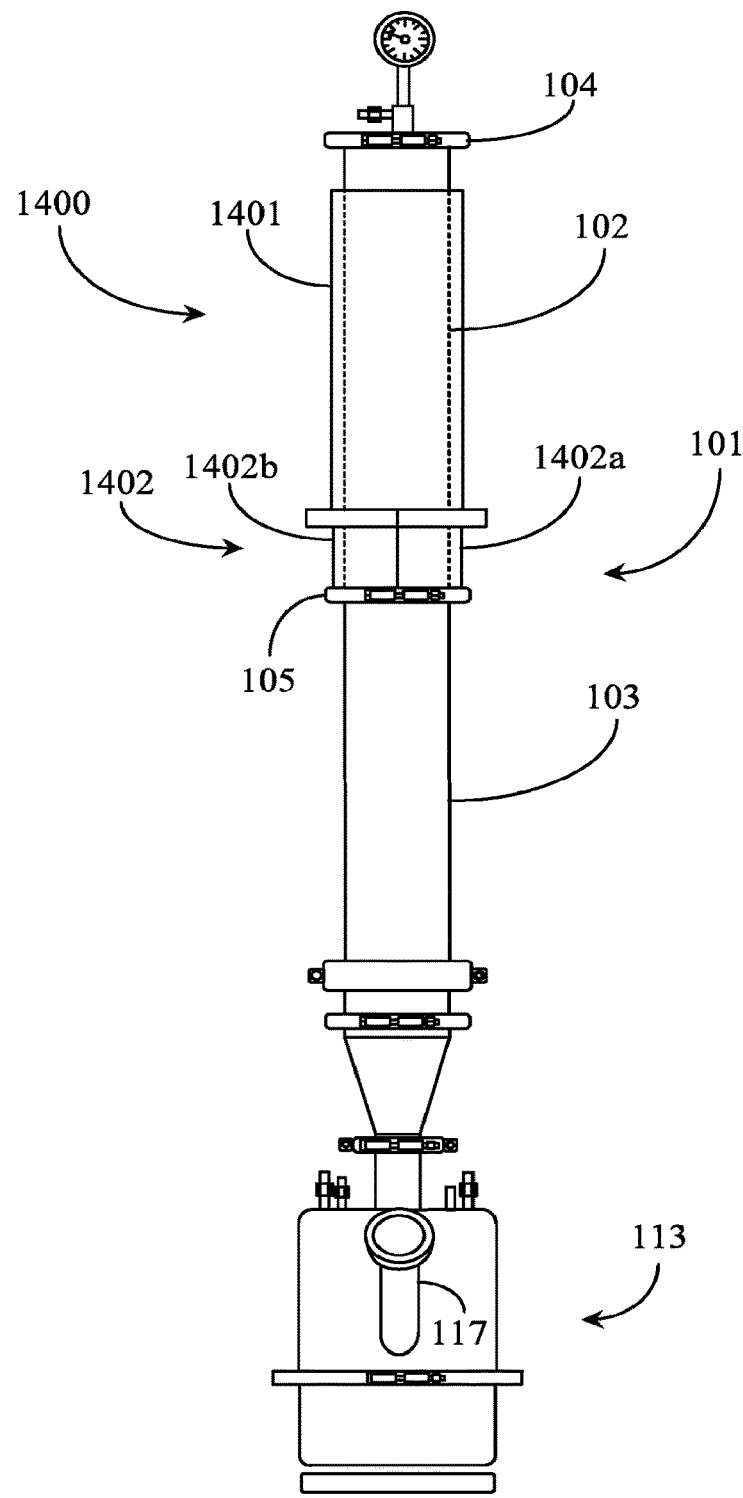
FIG. 14 is a front elevation view of the organic material processor 101 of FIG. 1 according to another embodiment of the present invention.

FIG. 14 is a front elevation view of the organic material processor 101 of FIG. 1 according to another embodiment of the present invention. Processor 101 is referred to herein as an extraction system or unit as described further above with reference to FIG. 1. In this implementation, the inventor provides a unique tubular ice sleeve 1401 that fits over container 102 in this example and seats onto a sleeve base 1402. Sleeve base 1402 comprises half parts 1402a and 1402b. Sleeve base 1402 may be fabricated or molded of nylon or another polymer type material. Sleeve 1401 fits into an annular recess on the surface of base 1402. Sleeve 1401 may be filled with dry ice or another cooling agent while material is being processed in order to cool down the material inside to freezing temperatures in order to aid in isolation of the lipids of the material. The density of the lipids causes them to break off of the host plant materials when they are cold.

Figure 15:
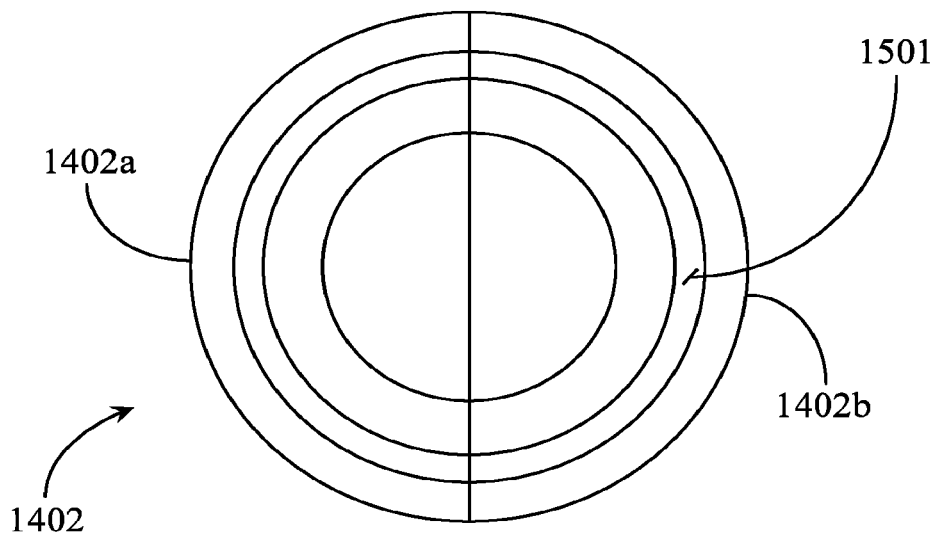
FIG. 15 is a top view of a sleeve base according to an embodiment of the present invention.

FIG. 15 is a top view of sleeve base 1402 according to an embodiment of the present invention. Sleeve base 1402 is annular and has two parts 1402a and 1402b. An annular recess or groove 1501 is provided concentrically on the surface of base 1402 to seat the ice sleeve.

Figure 16:
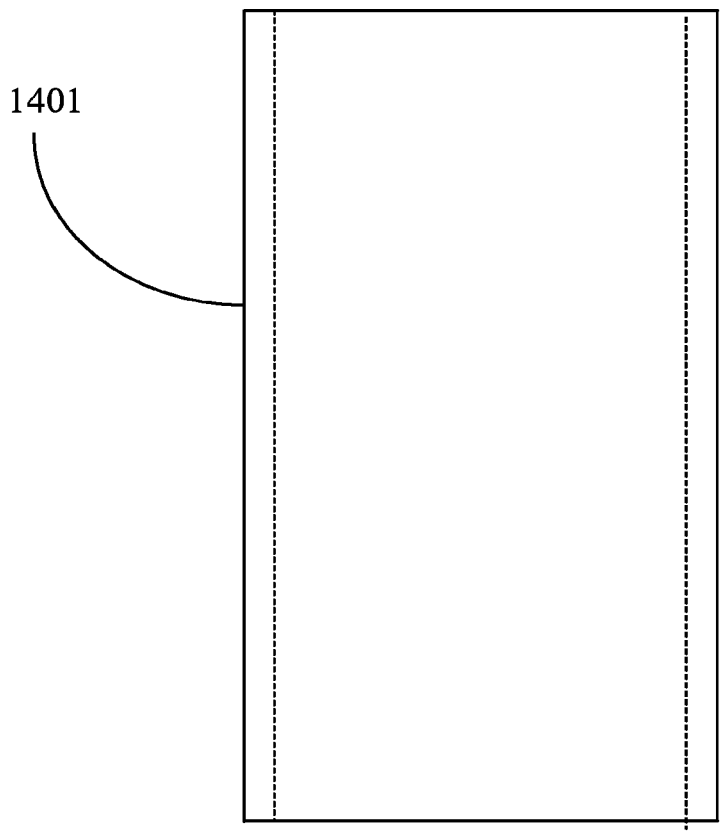
FIG. 16 is a side elevation view of an ice sleeve according to an embodiment of the present invention.

FIG. 16 is a side elevation view of ice sleeve 1401 according to an embodiment of the present invention. Ice sleeve 1401 may be a clear plastic or nylon sleeve open at both ends and having an inside diameter large enough to fit over the outside diameter of a process container, just making contact with an outside wall of the process container. The wall thickness of sleeve 1401 may be a nominal one eight of an inch or more to preserve rigidity of the sleeve when loaded with ice. Sleeve 1401 may be used with the modular container extraction system 100. It is noted herein that sleeve 1401 and base 1402 may be manufactured of different diameters to fit specific diameter systems.

Figure 17:
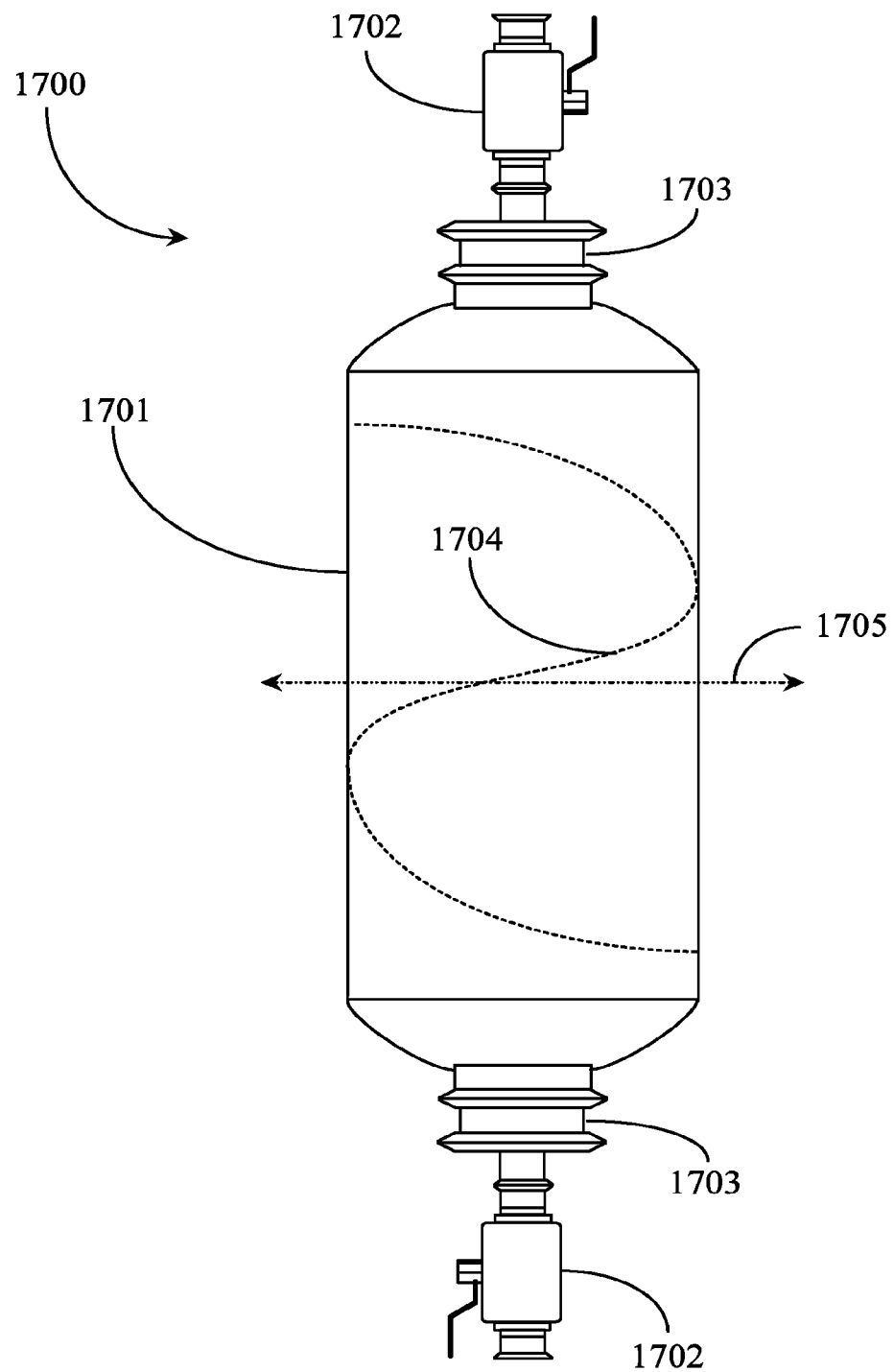
FIG. 17 is a front elevation view of a commercial organic material processor unit according to another embodiment of the present invention.

FIG. 17 is a front elevation view of a commercial organic material processor unit 1700 according to another embodiment of the present invention. Unit 1700 includes a chamber 1701 with a large diameter that may be used in the rotating mega system of FIG. 6 for example in place of mounted chamber 301. Chamber 1701 may be of a relative large diameter for commercial use, perhaps 16 inches or more for major diameter. Chamber 1701 includes a tube section 1703 of approximately 8 inches in diameter at both ends of the chamber. Tube section 1703 may contain or house an annular filter or baffle plate for directing/diffusing gas at ingress or for directing yield output at egress, as described in FIG. 7. Chamber 1701 may be fabricated of stainless steel like the other chambers and containers described herein.

Chamber 1701 includes a sphere valve assembly 1702 at opposite ends in this example. In this implementation, either end of chamber 1701 may be connected to a reducer assembly and a scope vessel (not illustrated). In this implementation, either end of chamber 1701 may be designated for connection to a reducer and scope vessel, as previously described. Also in this implementation the inside of chamber 1701 includes a baffle flute 1704 that aids in distribution of gas over the whole of the material more evenly.

It will be apparent to one with skill in the art that the organic material processing system and methods of the invention may be provided using some or all of the mentioned features and components without departing from the spirit and scope of the present invention. It will also be apparent to the skilled artisan that the embodiments described above are specific examples of a single broader invention which may have greater scope than any of the singular descriptions taught. There may be many alterations made in the descriptions without departing from the spirit and scope of the present invention.

It will further be apparent to the skilled person that the arrangement of elements and functionality for the invention is described in different embodiments in which each is exemplary of an implementation of the invention. These exemplary descriptions do not preclude other implementations and use cases not described in detail. The invention is limited only by the breadth of the claims below.

The invention claimed is:

1. An extraction system, comprising:
   an extraction chamber having a hollow inner volume, an end cap at one end of the extraction chamber enabled to accept organic matter into the chamber, and at least one inlet valve at a second end, opposite the one end, enabled to inject a gas or liquid solvent into the inner volume;
   a frame structure having a first and second axle, one each fixedly mounted on opposite sides of the extraction chamber at a balanced center point along a length between the one end and second end of the extraction chamber, said axles supported by the frame structure enabled to hold the chamber at a height from ground enabling free rotation of the chamber about the axles;
   wherein after introduction of the organic matter into the extraction chamber, with the end cap sealed, first ingress and egress fittings are connected via a conduit and extraction solvent is introduced in a quantity enabling at least lipid removal from the organic matter, said process influenced by translating the extraction chamber about the axis thereby macerating the organic matter, the solvent exiting the extraction chamber via the end cap.

2. The extraction system of claim 1, further including a collection vessel, centered and positioned below the end cap of the extraction chamber, the collection vessel having a closed lower end supported by a collection plate, and an open upper end enabled to connect to the end cap of the extraction chamber, and an interior volume enabled to collect a lipid yield.

3. The extraction system of claim 2, wherein a filter plate is positioned between the extraction chamber and collection vessel via an inlet opening removably attached to the end cap of the extraction chamber and an exit opening removably attached to the open upper end of the collection vessel, said filter removing contaminates from the yield.

4. The extraction system of claim 1 wherein a turn wheel is used to mechanically rotate the extraction chamber via the axles.

5. The extraction system of claim 2 wherein a gas introduction and recovery tank is provided with a first ingress fitting enabled to couple by conduit to a first egress fitting positioned at the upper end of the collection vessel to recover used extraction gas, and a second egress fitting on the tank enabled to connect by conduit to the at least one inlet valve introducing gas from the gas introduction and recovery tank into the extraction chamber.

6. The extraction system of claim 2 wherein a temperature controlled heater is positioned adjacent to and directly below the collection plate aiding in removal of at least gas and water contaminates from the yield.

7. The extraction system of claim 5 wherein the extraction chamber, collection vessel and collection plate are heated, alternately, to aid in moving and extracting used gas from the system into the gas introduction and recovery tank.

8. The extraction system of claim 5 wherein recovery of the extraction gas occurs simultaneously with collection of the lipid yield at the collection plate.

9. The extraction system of claim 4, wherein a vacuum pump is connected to a second conduit between a second ingress and egress fittings in order to aid in gas recovery.

10. The extraction system of claim 2 wherein a viewing vessel is provided with an open lower end sealed at an angle to an upper portion of a sidewall of the collection vessel, the viewing vessel having an open upper end and an elongated viewing tube through the sidewall ending at a viewing port with a lens, the viewing tube enables visual inspection through the lens and tube of the interior volume of the collection vessel at the collection plate.

11. The extraction system of claim 10, wherein the angle of attachment of the viewing vessel is an acute angle, enabling the open upper end to extend outwards and upwards toward the open upper end of the collection vessel.

12. The extraction system of claim 10, wherein when all components are connected, a closed system is created that is enabled to hold a negative or positive atmospheric pressure.

13. A method for extracting lipids from organic matter, comprising the steps of:
   (a) placing organic matter within a hollow inner volume of an extraction chamber having an end cap at one end, an inlet valve at a second end, opposite the one end, enabled to inject a gas or liquid solvent into the inner volume;
   (b) sealing the end cap with clamp and gasket assemblies achieving an airtight extraction chamber and introducing a gas solvent to the inner volume by coupling conduit to an ingress fitting at the inlet valve from a first egress fitting connected to a tank holding a reserve of solvent;
   (c) removing the ingress fitting from the inlet valve and agitating and macerating the organic matter and solvent by rotating the extraction chamber via a first and second axle one each fixedly mounted on opposite sides of the extraction chamber at a balanced center point along a length between upper and lower ends of the extraction chamber, said axles supported by a frame enabled to hold the chamber at a height from ground enabling free rotation of the chamber about the axles;
   (d) collecting the solvent and lipid yield from the extraction chamber.

14. The method of claim 13, wherein in step (d) collection occurs by connecting the end cap to an open upper end of a collection vessel, said collection vessel including a collection plate at a base of the collection vessel.

15. The method of claim 12, wherein a step for filtering the solvent and lipid yield is provided by positioning a filter plate between the extraction chamber and collection vessel via an inlet opening removably attached to the end cap of the extraction chamber and an exit opening removably attached to the open upper end of the collection vessel, said filter removing contaminates from the yield.

16. The method of claim 13 wherein a turn wheel is used to mechanically rotate the extraction chamber via the axles.

17. The method of claim 14 wherein a gas introduction and recovery tank is provided with a first ingress fitting enabled to couple by conduit to a first egress fitting positioned at the open upper end of the collection vessel to recover used extraction gas in step (d), and a second egress fitting on the tank enabled to connect by conduit to the at least one inlet valve introducing gas from the gas introduction and recovery tank into the extraction chamber in step (b).

18. The method of claim 17 wherein the extraction chamber, collection vessel and collection plate are heated, alternately, to aid in moving and extracting used gas from the system.

19. The method of claim 17, wherein a vacuum pump is connected to the conduit between the second ingress and egress fittings in order to aid in gas recovery.

20. The method of claim 14 wherein a viewing vessel is provided with an open lower end sealed at an angle to an upper portion of a sidewall of the collection vessel, the viewing vessel having an open upper end and an elongated viewing tube through the sidewall ending at a viewing port with a lens, the viewing tube enables visual inspection through the lens and tube of the interior volume of the collection vessel at the collection plate.

21. The method of claim 18, wherein the angle of attachment of the viewing vessel is an acute angle enabling the open upper end to extend outwards and upwards toward the open upper end of the collection vessel.

22. The method of claim 17, wherein when all components are connected, a closed system is created that is enabled to hold a negative or positive atmospheric pressure.

* * * * *